US006977154B1

(12) United States Patent
Choo et al.

(10) Patent No.: US 6,977,154 B1
(45) Date of Patent: Dec. 20, 2005

(54) NUCLEIC ACID BINDING PROTEINS

(75) Inventors: Yen Choo, Cambridge (GB); Mark Isalan, London (GB)

(73) Assignee: Gendaq Limited, London (GB)

( * ) Notice: Subject to any disclaimer, the term of this patent is extended or adjusted under 35 U.S.C. 154(b) by 0 days.

(21) Appl. No.: 09/646,353

(22) PCT Filed: Mar. 17, 1999

(86) PCT No.: PCT/GB99/00816

§ 371 (c)(1),
(2), (4) Date: Nov. 27, 2000

(87) PCT Pub. No.: WO99/47656

PCT Pub. Date: Sep. 23, 1999

(30) Foreign Application Priority Data

Mar. 17, 1998 (GB) ............................................. 9805576
Mar. 31, 1998 (GB) ............................................. 9806895
Apr. 3, 1998 (GB) ............................................. 9807246

(51) Int. Cl.[7] ............................................. G01N 33/53
(52) U.S. Cl. ............................. 435/7.1; 435/6; 435/4; 536/23.1; 530/350
(58) Field of Search .................. 435/7.1, 6, 4; 530/350; 636/23.1

(56) References Cited

U.S. PATENT DOCUMENTS

| 4,990,607 A | 2/1991 | Katagiri et al. |
| 5,096,814 A | 3/1992 | Aivasidis et al. |
| 5,096,815 A | 3/1992 | Ladner et al. |
| 5,198,346 A | 3/1993 | Ladner et al. |
| 5,223,409 A | 6/1993 | Ladner et al. |
| 5,243,041 A | 9/1993 | Fernandez-Pol |
| 5,302,519 A | 4/1994 | Blackwood et al. |
| 5,324,638 A | 6/1994 | Tao et al. |
| 5,324,818 A | 6/1994 | Nabel et al. |
| 5,324,819 A | 6/1994 | Oppermann et al. |
| 5,340,739 A | 8/1994 | Stevens et al. |
| 5,348,864 A | 9/1994 | Barbacid |
| 5,350,840 A | 9/1994 | Call et al. |
| 5,356,802 A | 10/1994 | Chandrasegaran |
| 5,376,530 A | 12/1994 | De The et al. |
| 5,403,484 A | 4/1995 | Ladner et al. |
| 5,436,150 A | 7/1995 | Chandrasegaran |
| 5,487,994 A | 1/1996 | Chandrasegaran |
| 5,498,530 A | 3/1996 | Schatz et al. |
| 5,578,483 A | 11/1996 | Evans et al. |
| 5,597,693 A | 1/1997 | Evans et al. |
| 5,639,592 A | 6/1997 | Evans et al. |
| 5,674,738 A | 10/1997 | Abramson et al. |
| 5,702,914 A | 12/1997 | Evans et al. |
| 5,789,538 A | 8/1998 | Rebar et al. |
| 5,792,640 A | 8/1998 | Chandrasegaran |
| 5,869,618 A | 2/1999 | Lippman et al. |
| 5,871,902 A | 2/1999 | Weininger et al. |
| 5,871,907 A | 2/1999 | Winter et al. |
| 5,916,794 A | 6/1999 | Chandrasegaran |
| 5,939,538 A | 8/1999 | Leavitt et al. |
| 5,972,615 A | 10/1999 | An et al. |
| 6,001,885 A | 12/1999 | Vega et al. |
| 6,007,988 A | 12/1999 | Choo et al. |
| 6,013,453 A | 1/2000 | Choo et al. |

FOREIGN PATENT DOCUMENTS

| WO | WO 95/19431 | 7/1995 |
| WO | WO 96/06110 | 2/1996 |
| WO | WO 96 06166 | 2/1996 |
| WO | WO 96/11267 | 4/1996 |
| WO | WO 96/20951 | 7/1996 |
| WO | WO 96/32475 | 10/1996 |
| WO | WO 97/27212 | 7/1997 |
| WO | WO 97/27213 | 7/1997 |
| WO | WO 98 53057 | 11/1998 |
| WO | WO 98 53058 | 11/1998 |
| WO | WO 98 53059 | 11/1998 |
| WO | WO 98 53060 | 11/1998 |
| WO | WO 98/54311 | 12/1998 |
| WO | WO 99/36553 | 7/1999 |
| WO | WO 99/41371 | 8/1999 |
| WO | WO 99/42474 | 8/1999 |
| WO | WO 99/45132 | 9/1999 |
| WO | WO 99/47656 | 9/1999 |
| WO | WO 99/48909 | 9/1999 |
| WO | WO 00/23464 | 4/2000 |
| WO | WO 00/27878 | 5/2000 |

OTHER PUBLICATIONS

Agarwal et al., "Stimulation of Transcript Elongation Requires both the Zinc Finger and RNA Polymerase II Binding Domains of Human TFIIS," *Biochemistry*, 30(31):7842–7851 (1991).

Anato et al., "A thermodynamic study of unusually stable RNA and DNA hairpins," *Nuc. Acids. Res.*, 19(21):5901–5905 (1991).

Barbas, C. F., "Recent advances in phage display," *Curr. Opin. Biotech.*, 4:526–530 (1993).

Barbas et al., "Assembly of combinatorial antibody libraries on phage surfaces: The gene III site," *PNAS*, 88:7978–7982 (1991).

Barbas et al., "Semisynthetic combinatorial antibody libraries: A chemical solution to the diversity problem," *PNAS*, 89:4457–4461 (1992).

Beerli et al., "Toward controlling gene expression at will; Specific regulation of the erbB–2/HER–2 promoter by using polydactyl zinc finger proteins constructed from modular building blocks," *PNAS*, 95:14628–14633 (1998).

(Continued)

Primary Examiner—T. D. Wessendorf
(74) Attorney, Agent, or Firm—Townsend and Townsend and Crew LLP

(57) ABSTRACT

The invention provides a method for producing a zinc finger polypeptide which binds to a target nucleic acid sequence containing a modified base but not to an identical sequence containing an equivalent unmodified base.

7 Claims, 7 Drawing Sheets

OTHER PUBLICATIONS

Bellefroid et al., "Clustered organization of homologous KRAB zinc–finger genes with enhanced expression in human T lymphoid cells," *EMBO J.*, 12(4):1363–1374 (1993).

Berg, J. M., "DNA Binding Specificity of Steriod Receptors," *Cell*, 57:1065–1068 (1989).

Berg, J. M., "Sp1 and the subfamily of zinc finger proteins with guarine–rich binding sites," *PNAS*, 89:11109–11110 (1992).

Berg et al., "The Galvanization of Biology: A Growing Appreciation for the Roles of Zinc," *Science*, 271:1081–1085 (1996).

Berg, J.M., "Letting your fingers do the walking," *Nature Biotechnology*, 15:323 (1997).

Bergqvist et al., "Loss of DNA–binding and new transcriptional trans–activation function in polyomavirus large T–antigen with mutation of zinc finger motif," *Nuc. Acids. Res.*, 18(9):2715–2720 (1990).

Blaese et al., "Vectors in cancer therapy: how will they deliver?," *Cancer Gene Therapy*, 2(4):291–297 (1995).

Caponigro et al., "Transdominant gentic analysis of a growth control pathway," *PNAS*, 95:7508–7513 (1998).

Celenza et al., "A Yeast Gene That is Essential for Release from Glucose Repression Encodes a Protein Kinase," *Science*, 233:1175–1180 (1986).

Cheng et al., "Identification of Potential Target Genes for Adr1p through Characterization of Essential Nucleotides in UAS1," *Mol. Cellular Biol.*, 14(6):3842–3852 (1994).

Cheng et al., "A Single Amino Acid substitution in Zinc Finger 2 of Adr1p Changes its Binding Specificity at two Positions in UAS1," *J. Mol. Biol.*, 251:1–8 (1995).

Choo et al., "A role in DNA binding for the linker sequences of the first three zinc fingers of TFIIIA," *Nuc. Acids Res.*, 21(15):3341–3346 (1993).

Choo et al., "All wrapped up," *Nature Structural Biology*, 5(4):253–255 (1998).

Choo et al., "Designing DNA–binding proteins on the surface of filamentous phage," *Curr. Opin. Biotechnology*, 6:431–436 (1995).

Choo, Y., "End effects in DNA recognition by zinc finger arrays," *Nuc. Acids Res.*, 26(2):554–557 (1998).

Choo et al., "In vivo repression by a site–specific DNA–binding protein designed against an oncogenic sequence," *Nature*, 372:642–645 (1994).

Choo et al., "Promoter–specific Activation of Gene Expression Directed by Bacteriophage–selected Zinc Fingers," *J. Mol. Biol.*, 273:525–532 (1997).

Choo et al., "Selection of DNA binding sites for zinc fingers using rationally randomized DNA reveals coded interactions," *PNAS*, 91:11168–11172 (1994).

Choo et al., "Toward a code for the interactions of zinc fingers with DNA: Selection of randomized fingers displayed on phage,". *PNAS*, 91:11163–11167 (1994).

Clarke et al., "Zinc Fingers in *Caenorhabditis elegans*: Finding Families and Probing Pathways," *Science*, 282:2018–2022 (1998).

Corbi, N. et al., "Synthesis of a New Zinc Finger Peptide; Comparison of its 'Code' Deduced and 'CASTing' Derived Binding Sites" *FEBS Letters*, 417:71–74 (1997).

Crozatier et al., "Single Amino Acid Exchanges in Separate Domains of the Drosophila serendipity δ Zinc Finger Protein Cause Embryonic and Sex Biased Lethality," *Genetics*, 131:905–916 (1992).

Debs et al., "Regulation of Gene Expression in Vivo by Liposome–mediated Delivery of a Purified Transcription Factor*," *J. Biological Chemistry*, 265(18):10189–10192 (1990).

Desjarlais et al., "Length–encoded multiplex binding site determination: Application to zinc finger proteins," *PNAS*, 91:11099–11103 (1994).

Desjarlais et al., "Use of a zinc–finger consensus sequence framework and specificity rules to design specific DNA binding proteins," *PNAS*, 90:2256–2260 (1993).

Desjarlais et al., "Toward rules relating zinc finger protein sequences and DNA binding site preferences," *PNAS*, 89(16):7345–7349 (1992).

Desjarlais et al., "Redesigning the DNA–Binding Specificity of a Zinc Finger Protein: A Data Base–Guided Approach," *Proteins: Structure, Function, and Genetics*, 12(2):101–104 (1992).

Desjarlais et al., "Redesigning the DNA–Binding Specificity of a Zinc–Finger Protein: A Data Base–Guided Approach," *Proteins: Structure, Function, and Genetics*, 13:272 (1992).

DiBello et al., "The Drosophila Broad–ComplexEncodes a Family of Related Proteins Containing Zinc Fingers," *Genetics*, 129:385–397 (1991).

Elrod–Erickson et al., "High–resolution structures of variant Zif268–DNA complexes: implications for understanding zinc finger–DNA recognition," *Structure*, 6(4):451–464 (1998).

Elrod–Erickson et al., "Zif268 protein–DNA complex refined at 1.6 Å: a model system for understanding zinc finger–DNA interactions," *Structure*, 4(10):1171–1180 (1996).

Fairall et al., "The crystal structure of a two zinc–finger peptide reveals an extension to the rules for zinc–finger/DNA recognition," *Nature*, 366:483–487 (1993).

Frankel et al., "Fingering Too Many Proteins," *Cell*, 53:675 (1988).

Friesen et al., "Phage Display of RNA Binding Zinc Fingers from Transcription Factor IIIA*," *J. Biological Chem.*, 272(17):10994–10997 (1997).

Friesen et al., "Specific FNA binding proteins constructed from zinc fingers," *Nature Structural Biology*, 5(7):543–546(1998).

Ghosh, D., "A relational database of transcription factors," *Nuc. Acids Res.*, 18(7):1749–1756 (1990).

Gorgos et al., "Recognition of diverse sequences by class I zinc fingers: Asymmetries and indirect effects on specificity in the interaction betwen CF2II and A+T–rich sequence elements," *PNAS*, 93(5):2159–2164 (1996).

Gossen et al., "Tight control of gene expression in mammalian cells by tetracycline–responsive promoters," *PNAS*, 89:5547–5551 (1992).

Greisman et al., "A General Strategy for Selecting High–Affinity Zinc Finger Proteins for Diverse DNA Target Sites," *Science*, 275;657–661 (1997).

Hamilton et al., "Comparison of the DNA Binding Characteristics of the Related Zinc Finger Proteins WT1 and EGR1," *Biochemistry*, 37:2051–2058 (1998).

Hamilton et al., "High affinity binding sites for the Wilms' tumor suppressor protein WT1," *Nuc. Acids Res.*, 23(2):277–284 (1995).

Hanas et al., "Internal deletion mutants of Xenopus transcription factor IIIA," *Nuc. Acids Res.*, 17(23):9861–9870 (1989).

Hayes et al., "Locations of Contacts between Individual Zinc Fingers of *Xenopus laevis* Transcription Factor IIIA and the Internal Control Region of a 5S RNA Gene," *Biochemistry*, 31:11600–11605 (1992).

Heinzel et al., "A complex containing N–CoR, mSin3 and histone deacetylase mediates transcriptional repression," *Nature*, 387:43–48 (1997).

Hirst et al., "Discrimination of DNA response elements for thyroid hormone and estrogen is dependant on dimerization of receptor DNA binding domains," *PNAS*, 89:5527–5531 (1992).

Hoffman et al., "Structures of DNA–binding mutant zinc finger domains: implications for DNA binding," *Protein Science*, 2:951–965 (1993).

Isalan et al., "Comprehensive DNA Recognition through Concerted Interactions from Adjacent Zinc Fingers," *Biochemistry*, 37:12026–12033 (1998).

Jacobs, G. H., "Determination of the base recognition positions of zinc fingers from sequence analysis," *EMBO J.*, 11(12):4507–4517 (1992).

Jamieson et al., "A zinc finger directory for high–affinity DNA recognition," *PNAS*, 93:12834–12839 (1996).

Jamieson et al., "In Vitro Selection of Zinc Fingers with Altered DNA–Binding Specificity," *Biochemistry*, 33(19):5689–5695 (1994).

Julian et al., "Replacement of His23 by Cys in a zinc finger of HIV–1 NCp7 led to a change in 1H NMR–derived 3D structure and to a loss of biological activity," *FEBS letters*, 331(1,2):43–48 (1993).

Kamiuchi et al., "New multi zinc finger protein: biosynthetic design and characteristics of DNA recognition," *Nucleic Acids Symposium Series*, 37:153–154 (1997).

Kang, J.S. et al., "Zinc Finger Proteins as Designer Transcription Factors," *J. Biol. Chem.*, 275(12):8742–8748 (2000).

Kim et al., "A 2.2 A° resolution crystal structure of a designed zinc finger protein bound to DNA," *Nat. Struct. Biol.*, 3(11):940–945 (1996).

Kim et al., "Design of TATA box–binding protein/zinc finger fusions for targeted regulation of gene expression," *PNAS*, 94:3616–3620 (1997).

Kim et al., "Getting a handhold on DNA: Design of poly–zinc finger proteins with femtomolar dissociation constants," *PNAS*, 95:2812–2817 (1998).

Kim et al., "Serine at Position 2 in the DNA Recognition helix of a Cys2–His2 Zinc finger Peptide is Not, in General, Responsible for Base Recognition," *J. Mol. Biol.*, 252:1–5 (1995).

Kim et al., "Site–specific cleavage of DNA–RNA hybrids by zinc finger/FokI cleavage domain fusions," *Gene*, 203:43–49 (1997).

Kim et al., "Transcriptional repression by zinc finger peptides," *J. Biol. Chem.*, 272(47):29795–28000 (1997).

Kinzler et al., "The GLI gene is a member of the Kruppel family of zinc finger proteins," *Nature*, 332:371–4 (1988).

Klug, A., "Gene Regulatory Proteins and Their Interaction with DNA," *Ann. NY Acad. Sci.*, 758:143–160 (1995).

Klug et al., "Protein Motifs 5: Zinc Fingers," *FASEB J.*, 9:597–604 (1995).

Klug, A., "Zinc Finger Peptides for the Regulation of Gene Expression," *J. Mol. Biol.*, 293:215–218 (1999).

Kothekar, V., "Computer simulation of zinc finger motifs from cellular nucleic acid binding protein and their interaction with consensus DNA sequences," *FEBS Letters*, 274(1–2):217–222 (1990).

Kriwacki et al., "Sequence–specific recognition of DNA by zinc–finger peptides dervied from the transcription factor Sp1," *PNAS*, 89:9759–9763 (1992).

Kulda et al., "The regulatory gene areA mediating ntirogen metabolite repression in *Aspergillus nidulans*. Mutations affecting specificity of gene activation after a loop residue of a putative zinc finger," *EMBO J.*, 9(5):1355–1364 (1990).

Laird–Offringa et al., "RNA–binding proteins tamed," *Nat. Structural Biol.*, 5(8):665–668 (1998).

Liu et al., "Design of polydactyl zinc–finger proteins for unique addressing within complex genomes," *PNAS*, 94(11):5525–5530 (1997).

Mandel–Gutfreund et al., "Quantitative parameters for amino acid–base interaction: implications for prediction of protein–DNA binding sites," *Nuc. Acids. Res.*, 26(10):2306–2312 (1998).

Margolin et al., "Kruppel–associated boxes are potent transcriptional repression domains," *PNAS*, 91:4509–4513 (1994).

Mizushima et al., "pEF–BOS, a powerful mammilian expression vector," *Nuc. Acids Res.*, 18(17):5322 (1990).

Nakagama et al., "Sequence and Structural Requirements for High-Affinity DNA Binding by the WT1 Gene Product," *Molecular and Cellular Biology*, 15(3):1489–1498 (1995).

Nardelli et al., "Zinc finger–DNA recognition: analysis of base specificity by site–directed mutagenesis," *Nuc. Acids Res.*, 20(16):4137–4144 (1992).

Nardelli et al., "Base sequence discrimination by zinc–finger DNA–binding domains," *Nature*, 349:175–178 (1991).

Nekludova et al., "Distinctive DNA conformation with enlarged major groove is found in Zn–finger—DNA and other protein—DNA complexes," *PNAS*, 91:6948–6952 (1994).

Orkin et al., "Report and Recommendations of the Panel to Assess the NIH Investment in Research on Gene Therapy," Dec. 7, 1995.

Pabo et al., "Protein–DNA Recognition," *Ann. Rev. Biochem.*, 53:293–321 (1984).

Pabo et al., "Systematic Analysis of Possible Hydrogen Bonds between Amino Acid Side Chains and B–form DNA," *J. Biomolecular Struct. Dynamics*, 1:1039–1049 (1983).

Pabo, C. O., "Transcription Factors: Structural Families and Principles of DNA Recognition," *Ann. Rev. Biochem.*, 61:1053–1095 (1992).

Pavletich et al., "Crystal Structure of a Five–Finger GLI–DNA Complex: New Perspectives on Zinc Fingers," *Science*, 261:1701–1707 (1993).

Pavletich et al., "Zinc Finger–DNA Recognition: Crystal Structure of a Zif268–DNA Complex at 2.1 Å," *Science*, 252:809–817 (1991).

Pengue et al., "Kruppel–associated box–mediated repression of RNA polymerase II promoters is influenced by the arrangement of basal promoter elements," *PNAS*, 93:1015–1020 (1996).

Pengue et al., "Repression of transcriptional activity at a distance by the evolutionarily conserved KRAB domain present in a subfamily of zinc finger proteins," *Nuc. Acids. Res.*, 22(15):2908–2914 (1994).

Pengue et al., "Transcriptional Silencing of Human Immunodeficiency Virus Type 1 Long Terminal Repeat–Driven Gene Expression by the Kruppel–Associated Box Repressor Domain Targeted to the Transactivating Response Element," *J. Virology*, 69(10):6577–6580 (1995).

Pomerantz et al., "Analysis of homeodomain function by structure–based design of a transcription factor," *PNAS*, 92:9752–9756 (1995).

Pomerantz et al., "Structure–Based Design of a Dimeric Zinc Finger Protein," *Biochemistry*, 37(4):965–970 (1998).

Pomerantz et al., "Structure–Based Design of Transcription Factors," *Science*, 267:93–96 (1995).

Qian et al., "Two–Dimensional NMR Studies of the Zinc Finger Motif: Solution Structures and Dynamics of Mutant ZFY Domains Containing Aromatic Substitutions in the Hydrophobic Core," *Biochemistry*, 31:7463–7476 (1992).

Quigley et al., "Complete Androgen Insensitivity Due to Deletion of Exon C of the Androgen Receptor Gene Highlights the Functional Importance of the Second Zinc Finger of the Androgen Receptor in Vivo," *Molecular Endocrinology*, 6(7):1103–1112 (1992).

Rauscher et al., "Binding of the Wilms' Tumor Locus Zinc Finger Protein to the EGR–1 Consensus Sequence," *Science*, 250:1259–1262 (1990).

Ray et al., "Repressor to activator switch by mutations in the first Zn finger of the glucocorticoid receptor: Is direct DNA binding necessary?," *PNAS*, 88:7086–7090 (1991).

Rebar et al., "Phage Display Methods for Selecting Zinc Finger Proteins with Novel DNA–Binding Specificities," *Methods in Enzymology*, 267:129–149 (1996).

Rebar et al., "Zinc Finger Phage: Affinity Selection of Fingers with New DNA–Binding Specificities," *Science*, 263:671–673 (1994).

Reith et al., "Cloning of the major histocompatibility complex class II promoter binding protein affected in a hereditary defect in class II gene regulation," *PNAS*, 86:4200–4204 (1989).

Rhodes et al., "Zinc Fingers: They play a key part in regulating the activity of genes in many species, from yeast to humans. Fewer than 10 years ago no one knew they existed," *Scientific American*, 268:56–65 (1993).

Rice et al., "Inhibitors of HIV Nucleocapsid Protein Zinc Fingers as Candidates for the Treatment of AIDS," *Science*, 270:1194–1197 (1995).

Rivera et al., "A humanized system for pharmacologic control of gene expression," *Nature Medicine*, 2(9):1028–1032 (1996).

Rollins et al., "Role of TFIIIA Zinc Fingers in vivo: Analysis of Single–Finger Function in Developing *Xenopus* Embryos," *Molecular Cellular Biology*, 13(8):4776–4783 (1993).

Sadowski et al., "GAL4–VP16 is an Unusually Potent Transcriptional Activator," *Nature*, 335:563–564 (1998).

Saleh et al., "A Novel Zinc Finger Gene on Human Chromosome 1qter That is Alternatively Spliced in Human Tissues and Cell Lines," *Am. J. Hum. Genet.*, 52:192–203 (1993).

Shi et al., "A direct comparison of the properties of natural and designed finger proteins," *Chem. & Biol.*, 2(2):83–89 (1995).

Shi et al., "DNA Unwinding Induced by Zinc Finger Protein Binding," *Biochemistry*, 35:3845–3848 (1996).

Shi et al., "Specific DNA–RNA Hybrid Binding by Zinc Finger Proteins," *Science*, 268:282–284 (1995).

Singh et al., "Molecular Cloning of an Enhancer Binding Protein: Isolation by Screening of an Expression Library with a Recognition Site DNA," *Cell*, 52:415–423 (1988).

Skerka et al., "Coordinate Expression and Distinct DNA–Binding Characteristics of the four EGR–Zinc Finger Proteins in Jukat T Lymphocytes," *Immunobiology*, 198:179–191 (1997).

South et al., "The Nucleocapsid Protein Isolated from HIV–1 Particles Binds Zinc and Forms Retroviral–Type Zinc Fingers," *Biochemistry*, 29:7786–7789 (1990).

Suzuki et al. "DNA recognition code of transcription factors in the helix–turn–helix, probe helix, hormone receptor, and zinc finger families," *PNAS*, 91:12357–12361 (1994).

Suzuki et al., "Stereochemical basis of DNA recognition by Zn fingers," *Nuc. Acids Res.*, 22(16):3397–3405 (1994).

Swirnoff et al., "DNA–Binding Specificity of NGFI–A and Related Zinc Finger Transcription Factors," *Mol. Cell. Biol.*, 15(4):2275–2287 (1995).

Taylor et al, "Designing Zinc–Finer ADR1 Mutants with Altered Specificity of DNA Binding to T in UAS1 Sequences," *Biochemistry*, 34:3222–3230 (1995).

Thiesen et al., "Amino Acid Substitutions in the SP1 Zinc Finger Domain Alter the DNA Binding Affinity to Cognate SP1 Target Site," *Biochem. Biophys. Res. Communications*, 175(1):333–338 (1991).

Thiesen et al., "Determination of DNA binding specificities of mutated zinc finger domains," *FEBS Letters*, 283(1):23–26 (1991).

Thukral et al., "Alanine scanning site–directed mutagenesis of the zinc fingers of transcription factor ADR1: Residues that contact DNA and that transactivate," *PNAS*, 88:9188–9192 (1991), + correction page.

Thukral et al., "Localization of a Minimal Binding Domain and Activation Regions in Yeast Regulatory Protein ADR1," *Molecular Cellular Biology*, 9(6):2360–2369 (1989).

Thukral et al., "Mutations in the Zinc Fingers of ADR1 That Change the Specificity of DNA Binding and Transactivation," *Mol. Cell Biol.*, 12(6):2784–2792 (1992).

Thukral et al., "Two Monomers of Yeast Transcription Factor ADR1 Bind a Palindromic Sequence Symmetrically to Activate ADH2 Expression," *Molecular Cellular Biol.*, 11(3):1566–1577 (1991).

Vortkamp et al., "Identificaton of Optimized Target Sequences for the GLI3 Zinc Finger Protein," *DNA Cell Biol.*, 14(7):629–634 (1995).

Wang, S.W. et al., "Dimerization of Zinc fingers Mediated by Peptides Evolved in vitro from Random Sequences," *PNAS*, 96: 9568–9573 (1999).

Webster et al., "Conversion of the E1A Cys4 zinc finger to a nonfunctional His2, Cys2 zinc finger by a single point mutation," *PNAS*, 88:9989–9993 (1991).

Whyatt et al., "The two zinc finger–like domains of GATA–1 have different DNA binding specificities," *EMBO J.*, 12(13):4993–5005 (1993).

Wilson et al., "In Vivo Mutational analysis of the NGFI–A Zinc Fingers", *J. Biol. Chem.*, 267(6):3718–3724 (92).

Witzgall et al., "The Kruppel–associated box–A (KRAB–A) domain of zinc finger proteins mediates transcriptional repression," *PNAS*, 91:4514–4518 (1994).

Wolfe, S.A. et al., "Analysis of Zinc Fingers Optimized via Phage Display: Evaluating the Utility of a Recognition Code," *J. Mol. Biol.*, 285:1917–1934 (1999).

Wright et al., "Expression of a Zinc Finger Gene in HTLV–I– and HTLV–II–transformed Cells," *Science*, 248:588–591 (1990).

Wu et al., "Building zinc fingers by selection: Toward a therapeutic application," *PNAS*, 92:344–348 (1995).

Yang et al., "Surface plasmon resonance based kinetic studies of zinc finger–DNA interactions," *J. Immunol. Methods*, 183:175–182 (1995).

Yu et al., "A hairpin ribozyme inhibits expression of diverse strains of human immunodeficiency virus type 1," *PNAS*, 90:6340–6344 (1993).

Choo: "Recognition of DNA methylation by zinc fingers", nol 5 no4, Apr. 1998 pp. 264–266 and XP002116419.

Isalan et al Synergy between adjacent zinc fingers in sequence–specific DNA recognition: Proceedings of the National Academy of Sciences of USA, No. 94, May 27m 1997 pp. 5617–5621 XP002075337 ISSN 002708424.

Kim et al: "Hybrid restriction enzymes: Zinc finger fusions to Fok I cleavage domain", Proc. Natl. Acad. Sci , vol. 93, No. 3, Feb. 6, 1996, pp. 1156–1160, XP002116423.

Choo et al: "physical basis of a protein–DNA recognition code", Current Opinion in Structural Biology, nol 1, No. 7, Feb. 1, 1997, pp. 117–125, XP002075338, ISSN 0959–440X.

Radtke et al: "Differential sensitivity of zinc finger transcription factors MTF–1, Sp1 and Krox–20 to CpG methylation of their binding sites"Biol. Chem. Hoppe–Seyler, vol. 337, Jan. 1996, pp. 47–56, XP002116420.

Sakatsume et al;, "Binding of THZif–1, a MAZ–like zinc finger protein to the nuclease–hypersensitive element in the promoter region of the c–myc protooncogene", J. Biol. Chem., col. 271, No. 49, Dec. 6, 1996, pp. 21322–31333, XPOO2116421, Am Soc Biochem Mol Biol Inc.

Xu et al: "Cytosine methylation targetted to pre–determined sequences", Nature Genetics, vol. 17, No. 4, Dec. 1997, pp. 376–378, XP002116422.

-1 1 2 3 4 5 6 7 8 9
    R A D Ⓐ L M V H K R
    R G D Ⓐ L T S H E R
    R V D Ⓐ L E A H R R
    R E D Ⓐ L I R H G K (iii) G C G G C G G C G

-1 1 2 3 4 5 6 7 8 9
    R G P Ⓓ L A R H G R
    R E D Ⓥ L I R H G K

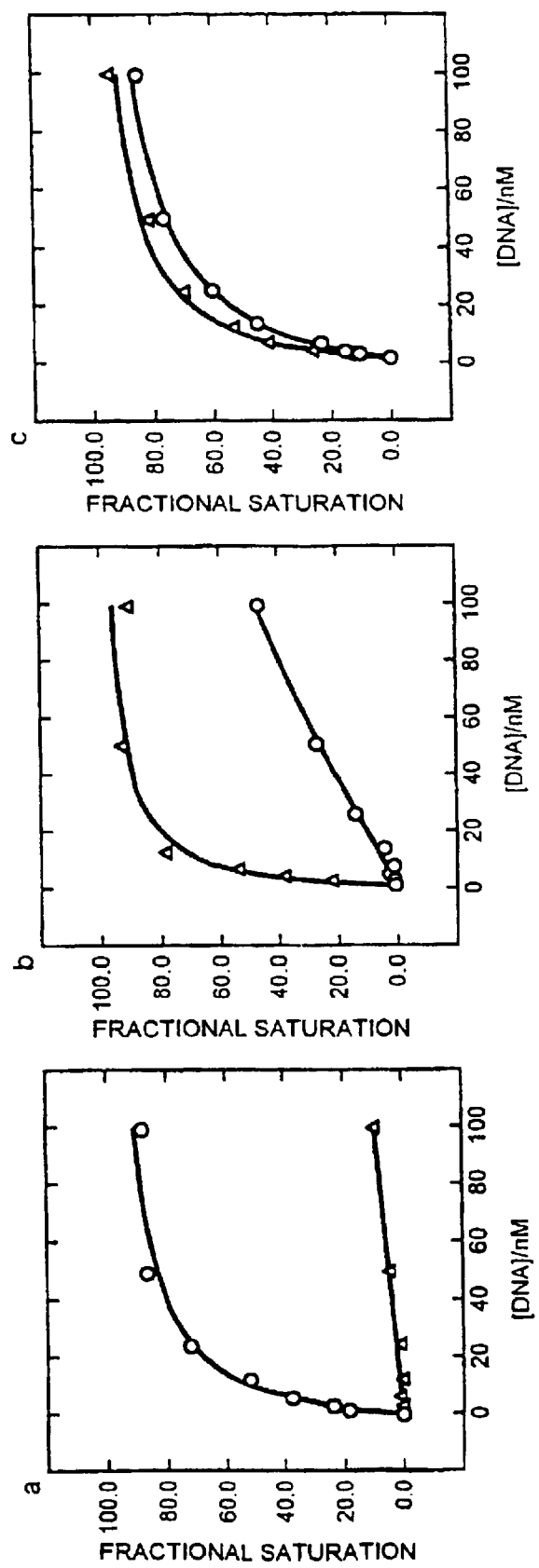

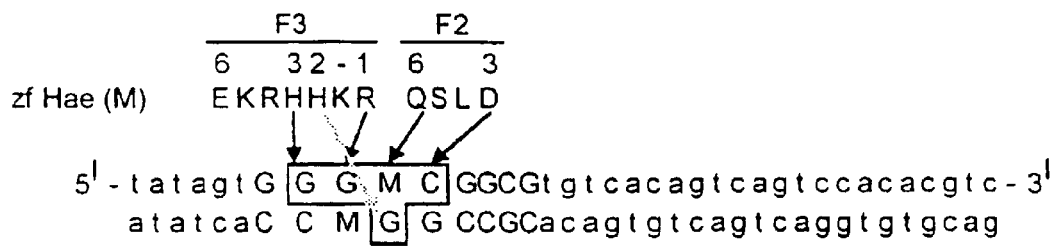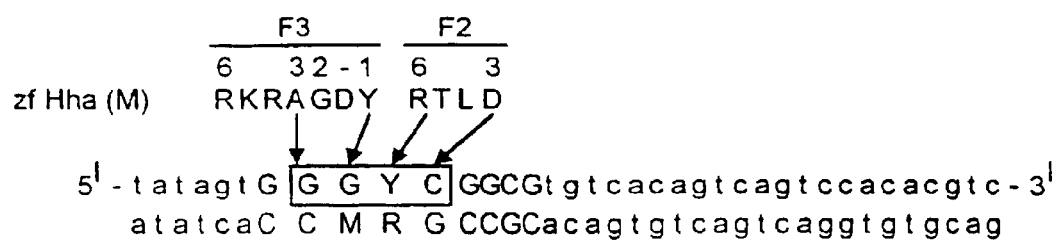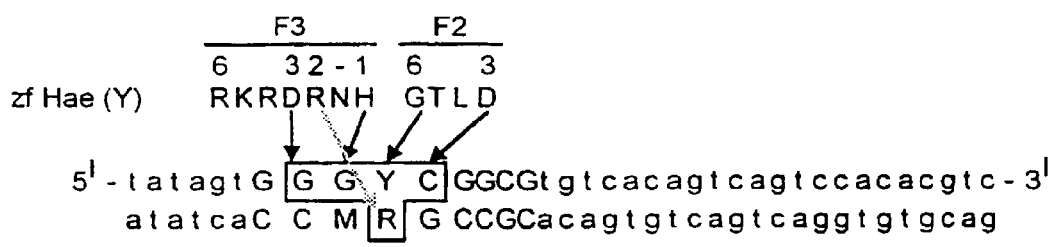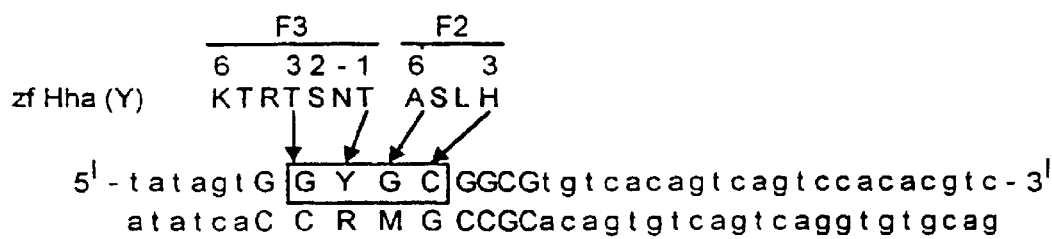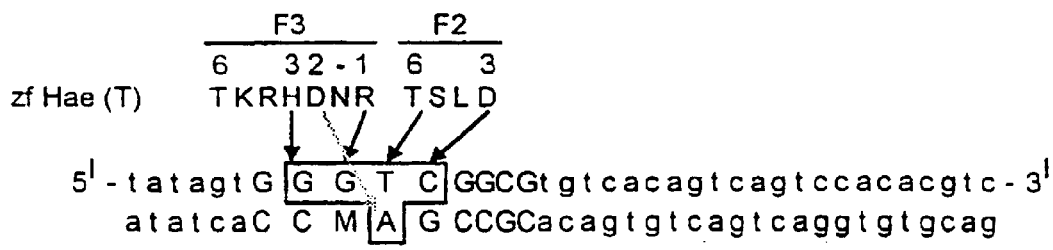
M=5-methylcytosine   Y=pyrimidine (C/T/M)   R=purine (A/G)
FIG. 3

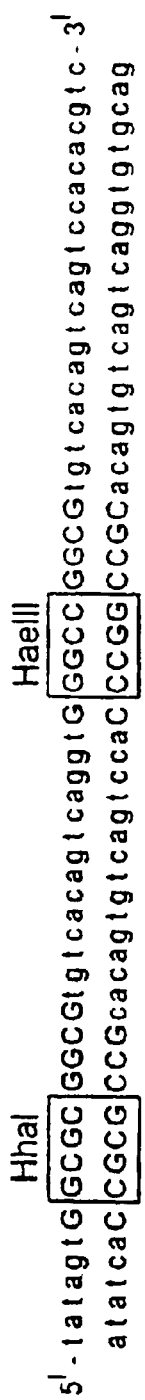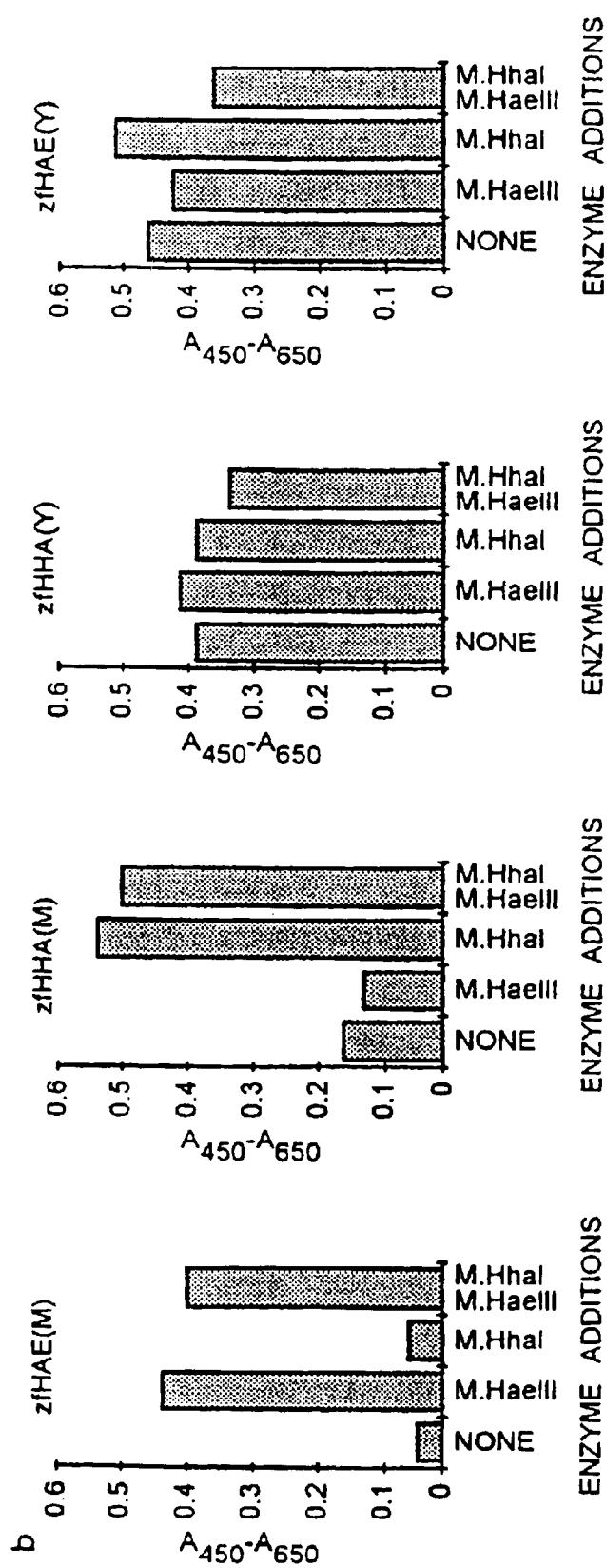
FIG. 6A
FIG. 6B

NUCLEIC ACID BINDING PROTEINS

The present invention relates to DNA binding proteins. In particular, the invention relates to a method for designing a protein which is capable of binding to a defined methylated DNA sequence but not to an equivalent unmethylated DNA sequence.

Protein-nucleic acid recognition is a commonplace phenomenon which is central to a large number of biomolecular control mechanisms which regulate the functioning of eukaryotic and prokaryotic cells. For instance, protein-DNA interactions form the basis of the regulation of gene expression and are thus one of the subjects most widely studied by molecular biologists.

A wealth of biochemical and structural information explains the details of protein-DNA recognition in numerous instances, to the extent that general principles of recognition have emerged. Many DNA-binding proteins contain independently folded domains for the recognition of DNA, and these domains in turn belong to a large number of structural families, such as the leucine zipper, the "helix-turn-helix" and zinc finger families.

Despite the great variety of structural domains, the specificity of the interactions observed to date between protein and DNA most often derives from the complementarity of the surfaces of a protein α-helix and the major groove of DNA [Klug, (1993) Gene 135:83–92]. In light of the recurring physical interaction of α-helix and major groove, the tantalising possibility arises that the contacts between particular amino acids and DNA bases could be described by a simple set of rules; in effect a stereochemical recognition code which relates protein primary structure to binding-site sequence preference.

It is clear, however, that no code will be found which can describe DNA recognition by all DNA-binding proteins. The structures of numerous complexes show significant differences in the way that the recognition α-helices of DNA-binding proteins from different structural families interact with the major groove of DNA, thus precluding similarities in patterns of recognition. The majority of known DNA-binding motifs are not particularly versatile, and any codes which might emerge would likely describe binding to a very few related DNA sequences.

Even within each family of DNA-binding proteins, moreover, it has hitherto appeared that the deciphering of a code would be elusive. Due to the complexity of the protein-DNA interaction, there does not appear to be a simple "alphabetic" equivalence between the primary structures of protein and nucleic acid which specifies a direct amino acid to base relationship.

International patent application WO 96/06166 addresses this issue and provides a "syllabic" code which explains protein-DNA interactions for zinc finger nucleic acid binding proteins. A syllabic code is a code which relies on more than one feature of the binding protein to specify binding to a particular base, the features being combinable in the forms of "syllables", or complex instructions, to define each specific contact.

Our copending UK patent applications, GB 9710805.4, 9710806.2, 9710807.0, 9710808.8, 9710809.6, 9710810.4, 9710811.2 and 9710812.0 describe improved techniques for designing zinc finger polypeptides capable of binding desired nucleic acid sequences. In combination with selection procedures, such as phage display, set forth for example in WO 96/06166, these techniques enable the production of zinc finger polypeptides capable of recognising practically any desired sequence.

Zinc finger domains studied and produced to date are capable of binding to recognition sequences composed by any of four nucleic acid bases: A, C, G or T (U in RNA). However, the DNA of many organisms includes also a fifth base, 5-methylcytosine (5-meC or, in nucleotide sequences herein, M). 5-meC arises from specific methylation of cytosine, and is used to mark the genome or to increase its information content. 5-methylcytosine is well known to affect protein-DNA interactions, for instance inhibiting cleavage of DNA by certain restriction enzymes. In vertebrates, cytosine is frequently methylated when directly preceding guanine, as in the dinucleotide CpG. This type of methylation generally down-regulates vertebrate gene expression, and can also prevent the binding of many eukaryotic transcription factors to DNA. Yet the zinc finger transcription factors tested to date, Sp1 and YY1, are not affected by CpG methylation of their DNA binding sites, suggesting that zinc fingers are incapable of discriminating between cytosine and 5-meC.

Since methylated cytosine bases are involved with many regulatory interactions in gene expression, and particularly in eukaryotic, including human, gene expression, the production of zinc finger polypeptides which specifically target methylated cytosine bases would be highly desirable. Such polypeptides, in order to be useful, must be able to differentiate DNA sequences in which cytosine is methylated to 5-meC from identical non-methylated sequences.

Further nucleic acid base modifications are known in the art. For example, brominated nucleosides are known, such as Br-dU. Being photolabile, brominated nucleosides are useful in the determination of DNA-protein complex structure. Br-dU containing oligonucleotides are also useful as probes, since antibodies are available which recognise Br-dU. Moreover, in antisense oligonucleotide chemnistry, the use of backbone modifications to improve oligonucleotide stability is well known; for example, phosphorothioate and 2'-O methylation are commonplace. Such backbone-modified nucleosides, and other nucleosides, may also be C-5 modified. For example, C-5 propyne derivatives and C-5 methylpyrimidine nucleosides are known and used in antisense nucleic acid chemistry.

Specific detection of modified nucleotides, and preferential binding of DNA-binding proteins thereto, is desirable. However, agents which are capable of reliably targeting a protein to a modified nucleic acid in a sequence-specific manner are not available in the art.

SUMMARY OF THE INVENTION

We have now determined that modified nucleosides can be specifically recognised, over unmodified equivalents, by zinc finger polypeptides in a sequence-dependent manner. The invention accordingly provides a method for producing a zinc finger polypeptide which binds to a target nucleic acid sequence containing a modified nucleic acid base, but not to an identical sequence containing the equivalent unmodified base.

In the present invention, a "modified" base is a nucleic acid base other than A, C, G or T as they occur in DNA in nature. Thus, the term modified includes methylated bases, such as 5-meC which occurs naturally in DNA, and base analogues, including naturally-occurring analogues such as U and artificial analogues such as I, backbone-modified bases and other artificial nucleosides.

In a first embodiment, the invention provides a method for preparing a DNA binding polypeptide of the Cys2-His2 zinc finger class capable of binding to a DNA triplet in target DNA sequence comprising 5-meC as the central residue in the target DNA triplet, wherein binding to the 5-meC residue by an α-helical zinc finger DNA binding motif of the polypeptide is achieved by placing an Ala residue at position +3 of the α-helix of the zinc finger.

All of the DNA-binding residue positions of zinc fingers, as referred to herein, are numbered from the first residue in the α-helix of the finger, ranging from +1 to +9. "−1" refers to the residue in the framework structure immediately preceding the α-helix in a Cys2-His2 zinc finger polypeptide. Residues referred to as "++" are residues present in an adjacent (C-terminal) finger. Where there is no C-terminal adjacent finger, "++" interactions do not operate.

Cys2-His2 zinc finger binding proteins, as is well known in the art, bind to target nucleic acid sequences via α-helical zinc metal atom coordinated binding motifs known as zinc fingers. Each zinc finger in a zinc finger nucleic acid binding protein is responsible for determining binding to a nucleic acid triplet in a nucleic acid binding sequence. Preferably, there are 2 or more zinc fingers, for example 2, 3, 4, 5 or 6 zinc fingers, in each binding protein. Advantageously, there are 3 zinc fingers in each zinc finger binding protein.

The method of the present invention allows the production of what are essentially artificial DNA binding proteins. In these proteins, artificial analogues of amino acids may be used, to impart the proteins with desired properties or for other reasons. Thus, the term "amino acid", particularly in the context where "any amino acid" is referred to, means any sort of natural or artificial amino acid or amino acid analogue that may be employed in protein construction according to methods known in the art. Moreover, any specific amino acid referred to herein may be replaced by a functional analogue thereof, particularly an artificial functional analogue. The nomenclature used herein therefore specifically comprises within its scope functional analogues of the defined amino acids.

The α-helix of a zinc finger binding protein aligns antiparallel to the nucleic acid strand, such that the primary nucleic acid sequence is arranged 3' to 5' in order to correspond with the N terminal to C-terminal sequence of the zinc finger. Since nucleic acid sequences are conventionally written 5' to 3', and amino acid sequences N-terminus to C-terminus, the result is that when a nucleic acid sequence and a zinc finger protein are aligned according to convention, the primary interaction of the zinc finger is with the − strand of the nucleic acid, since it is this strand which is aligned 3' to 5'. These conventions are followed in the nomenclature used herein. It should be noted, however, that in nature certain fingers, such as finger 4 of the protein GLI, bind to the + strand of nucleic acid: see Suzuki et al., (1994) NAR 22:3397–3405 and Pavletich and Pabo, (1993) Science 261:1701–1707. The incorporation of such fingers into DNA binding molecules according to the invention is envisaged.

The invention provides a solution to a problem hitherto unaddressed in the art, by permitting the rational design of polypeptides which will bind DNA triplets containing a 5-meC residue, but not identical triplets containing a C residue.

The present invention may be integrated with the rules set forth for zinc finger polypeptide design in our copending UK patent applications listed above. In a preferred aspect, therefore, the invention provides a method for preparing a DNA binding polypeptide of the Cys2-His2 zinc finger class capable of binding to a DNA triplet in target DNA sequence comprising 5-meC, but not to an identical triplet comprising unmethylated C, wherein binding to each base of the triplet by an α-helical zinc finger DNA binding motif in the polypeptide is determined as follows:

a) if the 5' base in the triplet is G, then position +6 in the α-helix is Arg and/or position ++2 is Asp;
b) if the 5' base in the triplet is A, then position +6 in the α-helix is Gln or Glu and ++2 is not Asp;
c) if the 5' base in the triplet is T, then position +6 in the α-helix is Ser or Thr and position ++2 is Asp; or position +6 is a hydrophobic amino acid other than Ala;
d) if the 5' base in the triplet is C, then position +6 in the α-helix may be any amino acid, provided that position ++2 in the α-helix is not Asp;
e) if the central base in the triplet is G, then position +3 in the α-helix is His;
f) if the central base in the triplet is A, then position +3 in the α-helix is Asn;
g) if the central base in the triplet is T, then position +3 in the α-helix is Ala, Ser, Ile, Leu, Thr or Val; provided that if it is Ala, then one of the residues at −1 or +6 is a small residue;
h) if the central base in the triplet is 5-meC, then position +3 in the α-helix is Ala, Ser, Ile, Leu, Thr or Val; provided that if it is Ala, then one of the residues at −1 or +6 is a small residue;
i) if the 3' base in the triplet is G, then position −1 in the α-helix is Arg;
j) if the 3' base in the triplet is A, then position −1 in the α-helix is Gln and position +2 is Ala;
k) if the 3' base in the triplet is T, then position −1 in the α-helix is Asn; or position −1 is Gln and position +2 is Ser;
l) if the 3' base in the triplet is C, then position −1 in the α-helix is Asp and position +1 is Arg.

The foregoing represents a set of rules which permits the design of a zinc finger binding protein specific for any given DNA sequence incorporating 5-meC.

A zinc finger binding motif is a structure well known to those in the art and defined in, for example, Miller et al., (1985) EMBO J. 4:1609–1614; Berg (1988) PNAS (USA) 85:99–102; Lee et al., (1989) Science 245:635–637; see International patent applications WO 96/06166 and WO 96/32475, corresponding to U.S. Ser. No. 08/422,107, incorporated herein by reference.

In general, a preferred zinc finger framework has the structure (A) $X_{0-2}$ C $X_{1-5}$ C $X_{9-14}$ H $X_{3-6}$ H/C where X is any amino acid, and the numbers in subscript indicate the possible numbers of the residues represented by X.

In a preferred aspect of the present invention, zinc finger nucleic acid binding motifs may be represented as motifs having the following primary structure:

(B) $X^a$ C $X_{2-4}$ C $X_{2-3}$ F $X^c$ X X X X L X X H X X X $X^b$
    H—linker −1 1 2 3 4 5 6 7 8 9 wherein X (including $X^a$, $X^b$ and $X^c$) is any amino acid. $X_{2-4}$ and $X_{2-3}$ refer to the presence of 2 or 4, or 2 or 3, amino acids, respectively. The Cys and His residues, which together co-ordinate the zinc metal atom, are marked in bold text and are usually invariant, as is the Leu residue at position +4 in the α-helix.

Modifications to this representation may occur or be effected without necessarily abolishing zinc finger function, by insertion, mutation or deletion of amino acids. For example, it is known that the second His residue may be replaced by Cys (Krizek et al., (1991) J. Am. Chem. Soc. 113:4518–4523) and that Leu at +4 can in some circumstances be replaced with Arg. The Phe residue before $X_c$ may be replaced by any aromatic other than Trp. Moreover, experiments have shown that departure from the preferred structure and residue assignments for the zinc finger are tolerated and may even prove beneficial in binding to certain nucleic acid sequences. Even taking this into account, however, the general structure involving an α-helix co-ordinated by a zinc atom which contacts four Cys or His residues, is not altered. As used herein, structures (A) and (B) above are taken as an exemplary structure representing all zinc finger structures of the Cys2-His2 type.

Preferably, $X^a$ is F/γ-X or P-F/γ-X. In this context, X is any amino acid. Preferably, in this context X is E, K, T or S. Less preferred but also envisaged are Q, V, A and P. The remaining amino acids remain possible.

Preferably, $X_{2-4}$ consists of two amino acids rather than four. The first of these amino acids may be any amino acid, but S, E, K, T, P and R are preferred. Advantageously, it is P or R. The second of these amino acids is preferably E, although any amino acid may be used.

Preferably, $X^b$ is T or I.

Preferably, $X^c$ is S or T.

Preferably, $X_{2-3}$ is G-K-A, G-K-C, G-K-S or G-K-G, However, departures from the preferred residues are possible, for example in the form of M-R-N or M-R.

Preferably, the linker is (SEQ ID NO.: 41) T-G-E-K or (SEQ ID NO.: 3) T-G-E-K-P.

As set out above, the major binding interactions occur with amino acids −1, +3 and +6. Amino acids +4 and +7 are largely invariant. The remaining amino acids may be essentially any amino acids. Preferably, position +9 is occupied by Arg or Lys. Advantageously, positions +1, +5 and +8 are not hydrophobic amino acids, that is to say are not Phe, Trp or Tyr. Preferably, position ++2 is any amino acid, and preferably serine, save where its nature is dictated by its role as a ++2 amino acid for an N-terminal zinc finger in the same nucleic acid binding molecule.

In a most preferred aspect, therefore, bringing together the above, the invention allows the definition of every residue in a zinc finger DNA binding motif which will bind specifically to a given DNA triplet incorporating a 5-meC residue as the central residue in the triplet. Where targeting of a 5-meC containing sequence is desired, therefor, a suitable zinc finger can be constructed selecting a binding site such that 5-meC occurs at the centre of at least one base triplet thereof.

The code provided by the present invention is not entirely rigid: certain choices are provided. For example, positions +1, +5 and +8 may have any amino acid allocation, whilst other positions may have certain options: for example, the present rules provide that, for binding to a central T residue, any one of Ala, Ser or Val may be used at +3. In its broadest sense, therefore, the present invention provides a very large number of proteins which are capable of binding to every defined target DNA triplet incorporating 5-meC as the central residue and thereby any DNA binding site incorporating 5-meC.

Preferably, however, the number of possibilities may be significantly reduced. For example, the non-critical residues +1, +5 and +8 may be occupied by the residues Lys. Thr and Gln respectively as a default option. In the case of the other choices, for example, the first-given option may be employed as a default. Thus, the code according to the present invention allows the design of a single, defined polypeptide (a "default" polypeptide) which will bind to its target triplet.

In a further aspect of the present invention, there is provided a method for preparing a DNA binding protein of the Cys2-His2 zinc finger class capable of binding to a target DNA sequence incorporating 5-meC, comprising the steps of:

a) selecting a model zinc finger domain from the group consisting of naturally occurring zinc fingers and consensus zinc fingers; and b) mutating at least one of positions −1, +3, +6 (and ++2) of the finger as required by a method according to the present invention.

In general, naturally occurring zinc fingers may be selected from those fingers for which the DNA binding specificity is known. For example, these may be the fingers for which a crystal structure has been resolved: namely Zif 268 (Elrod-Erickson et al., (1996) Structure 4:1171–1180), GLI (Pavletich and Pabo, (1993) Science 261:1701–1707). Tramtrack (Fairall et al., (1993) Nature 366:483–487) and YY1 (Houbaviy et al., (1996) PNAS (USA) 93:13577–13582).

The naturally occurring zinc finger 2 in Zif 268 makes an excellent starting point from which to engineer a zinc finger and is preferred.

Consensus zinc finger structures may be prepared by comparing the sequences of known zinc fingers, irrespective of whether their binding domain is known. Preferably, the consesnsus structure is selected from the group consisting of the consensus structure PYKCPECGKSFSQKS-DLVKHQRTHTG (SEQ. ID NO.:1), and the consensus structure PYKCSECGKAFSQKSNLTRHQRIHTGEKP (SEQ ID NO.:2).

The consensuses are derived from the consensus provided by Krizek et al., (1991) J. Am. Chem. Soc. 113:4518–4523 and from Jacobs, (1993) PhD thesis, University of Cambridge, UK. In both cases, the linker sequences described above for joining two zinc finger motifs together, namely (SEQ ID NO.: 41) TGEK or (SEQ ID NO.: 3) TGEKP can be formed on the ends of the consensus. Thus, a P may be removed where necessary, or, in the case of the consensus terminating (SEQ ID NO.: 42) T G, E K (P) can be added.

When the nucleic acid specificity of the model finger selected is known, the mutation of the finger in order to modify its specificity to bind to the target DNA may be directed to residues known to affect binding to bases at which the natural and desired targets differ. Otherwise, mutation of the model fingers should be concentrated upon residues −1, +3, +6 and ++2 as provided for in the foregoing rules.

In order to produce a binding protein having improved binding, moreover, the rules provided by the present invention may be supplemented by physical or virtual modelling of the protein/DNA interface in order to assist in residue selection.

In a second embodiment, the invention provides a method for producing a zinc finger polypeptide capable of binding to a DNA sequence comprising a modified residue, but not to an identical sequence comprising an equivalent unmodified residue, comprising:

a) providing a nucleic acid library encoding a repertoire of zinc finger polypeptides, the nucleic acid members of the library being at least partially randomised at one or more of the positions encoding residues −1, 2, 3 and 6 of the α-helix of the zinc finger polypeptides;

b) displaying the library in a selection system and screening it against a target DNA sequence comprising the modified residue;

c) isolating the nucleic acid members of the library encoding zinc finger polypeptides capable of binding to the target sequence; and d) optionally, verifying that the zinc finger polypeptides do not bind significantly to a DNA sequence identical to the target DNA sequence but containing the unmodified residue in place of the modified residue.

Methods for the production of libraries encoding randomised polypeptides are known in the art and may be applied in the present invention. Randomisation may be total, or partial; in the case of partial randomisation, the selected codons preferably encode options for amino acids as set forth in the rules of the first embodiment of the present invention. Thus, the first and second embodiments may advantageously be combined.

Preferably, the modified residue is 5-meC and the unmodified residue is C. However, other modifications may be targeted by the method of the invention. For example, zinc finger polypeptides may be designed which specifically bind to nucleic acids incorporating the base U, in preference to the equivalent base T. An advantage of the second embodiment of the invention is that zinc finger polypeptides may be developed to bind to any DNA sequence incorporating a modified base, irrespective of its positioning in the target DNA triplet.

In a further preferred aspect, the invention comprises a method for producing a zinc finger polypeptide capable of binding to a DNA sequence comprising a modified residue, but not to an identical sequence comprising an equivalent unmodified residue, comprising:

a) providing a nucleic acid library encoding a repertoire of zinc finger polypeptides each possessing more than one zinc fingers, the nucleic acid members of the library being at least partially randomised at one or more of the positions encoding residues −1, 2, 3 and 6 of the α-helix in a first zinc finger and at one or more of the positions encoding residues −1, 2, 3 and 6 of the α-helix in a further zinc finger of the zinc finger polypeptides;

b) displaying the library in a selection system and screening it against a target DNA sequence comprising the modified residue;

c) isolating the nucleic acid members of the library encoding zinc finger polypeptides capable of binding to the target sequence; and d) optionally, verifying that the zinc finger polypeptides do not bind significantly to a DNA sequence identical to the target DNA sequence but containing the unmodified residue in place of the modified residue.

In this aspect, the invention encompasses library technology described in our copending International patent application WO98/53057, incorporated herein by reference in its entirety. WO98/53057 describes the production of zinc finger polypeptide libraries in which each individual zinc finger polypeptide comprises more than one, for example two or three, zinc fingers; and wherein within each polypeptide partial randomisation occurs in at least two zinc fingers.

This allows for the selection of the "overlap" specificity, wherein, within each triplet, the choice of residue for binding to the third nucleotide (read 3' to 5' on the + strand) is influenced by the residue present at position +2 on the subsequent zinc finger, which displays cross-strand specificity in binding. The selection of zinc finger polypeptides incorporating cross-strand specificity of adjacent zinc fingers enables the selection of nucleic acid binding proteins with a higher degree of specificity than is otherwise possible.

Advantageously, in order to derive the greatest benefit, the binding site is selected such that the modified base is in position 3 of one of the triplets, such that cross-strand specificity can be relied upon to contact the parallel strand in the corresponding position and introduce a further level of discrimination.

In a third embodiment, the present invention may be applied to the production of zinc finger polypeptides capable of binding to a DNA sequence comprising an unmethylated C residue, but not to an identical sequence comprising a 5-meC residue. This may be carried out by differential screening, as set forth above. Moreover, rules may be applied in addition to or instead of screening.

Where the central residue of a target triplet is C, the use of Asp at position +3 of a zinc finger polypeptide allows preferential binding to C over 5-meC.

BRIEF DESCRIPTION OF THE FIGURES

Figure 1A:
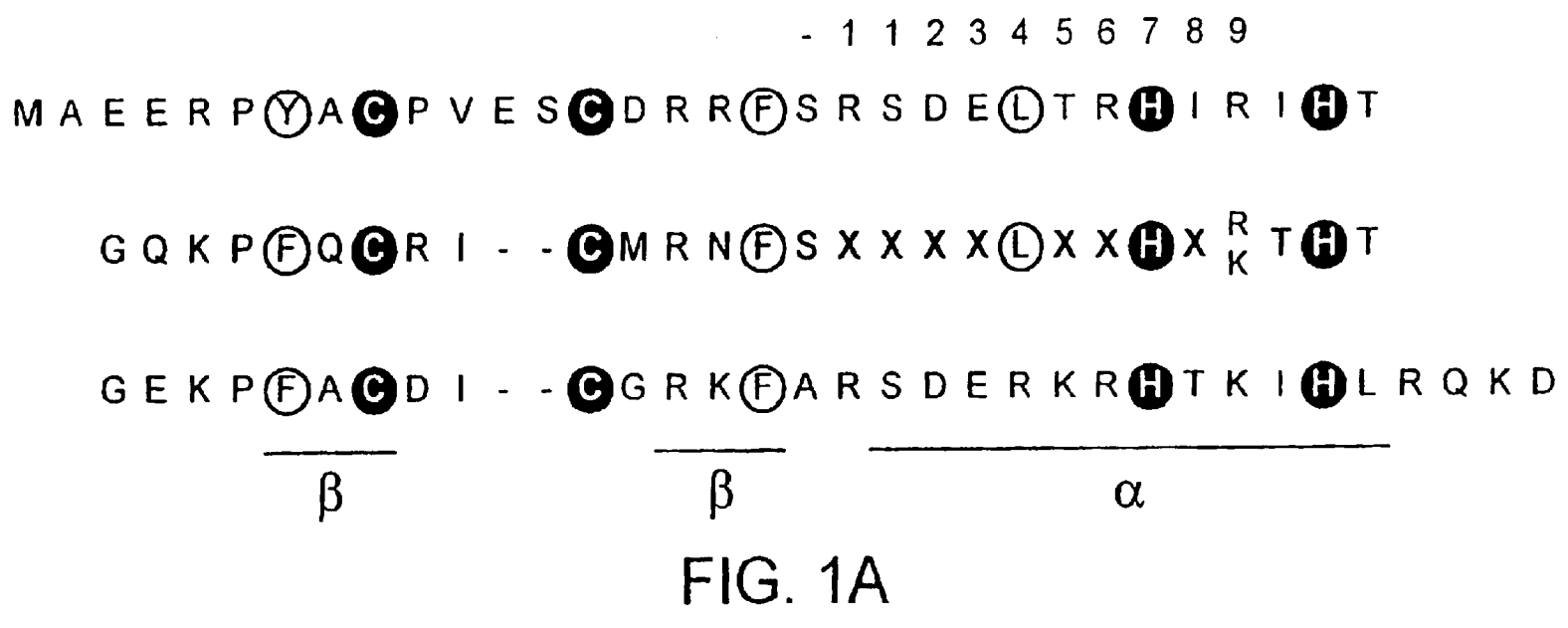

FIG. 1a is an alignment of the amino acid sequence of the three fingers (SEQ ID NOS.: 59–61, respectively in order of appearance) from Zif268 used in a phage display library. Randomised residue positions in the α-helix of finger 2 are marked 'X' and are numbered above the alignment relative to the first helical residue (position +1). Residues which form the hydrophobic core are circled; zinc ligands are written as white letters on a black circle background; and positions comprising the secondary structure elements of a zinc finger are marked below the sequence.

FIG. 2 shows the effect of cytosine methylation on DNA binding by phage-selected zinc fingers. Graphs show three different zinc finger phage binding to the DNA sequence (SEQ ID NO.:43) GCGGCGGCG in the presence (circle) and absence (triangle) of methylation of the central base (bold). The zinc finger clones tested contained variant α-helical regions of the middle finger as follows: (a) RADALMVHKR (SEQ ID NO.:6), (b) RGPDLARHGR (SEQ ID NO.:7 and (c) REDVLIRHGK (SEQ ID NO.:5). These respective zinc finger clones preferentially bind their cognate DNA site in the presence, absence, or regardless of cytosine methylation.

FIG. 3 shows the binding site interactions of 5 zinc finger polypeptides (SEQ ID NOS.: 65–66, 68–69, 71–72, 74–75, 77–78, respectively in order of appearance); selected taking into account cross-strand specificity by overlapping finger randomization, with each of the oligonucleotides used in the selection process. Cross-strand contacts are shown.

FIG. 6 shows binding of zinc finger polypeptides zfHHA (M) and zfHAE(M) to the nucleotide sequence (FIG. 6a) (SEQ ID NO:80) in response to selective methylation by addition of methylase enzymes (FIG. 6b). Polypeptides zfHHA(Y) and zfHAE(Y) do not discriminate between methylated and unmethylated DNA, as expected.

DETAILED DESCRIPTION OF THE INVENTION

Figures 1B, 1C:
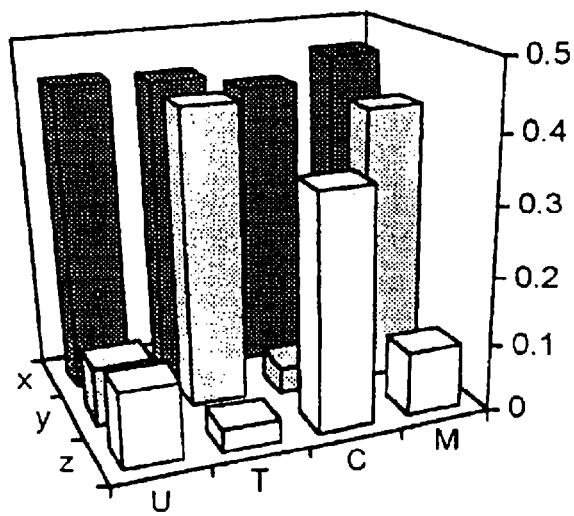
FIG. 1b shows amino acid sequences of the variant α-helical regions from some zinc fingers selected by phage display using the DNA binding site gcggnggcg (SEQ. ID NO.:4) where the central (bold) nucleotide of the middle (underlined) triplet was either (I) 5-methylcytosine, (ii) thymine, or (iii) cytosine. Amino acid sequences are listed below the DNA oligonucleotide used in their selection. Amino acid positions are numbered above the aligned sequences relative to the first helical residue (position +1). Circled residues (in position +3) are predicted to contact the middle nucleotide of the binding site.
FIG. 1c shows a phage ELISA binding assay showing discrimination of pyrimidines by representative phage-selected zinc fingers. The matrix shows three different zinc finger phage clones (x, y and z) reacted with four different DNA binding sites present at a concentration of 3 nM. Binding is represented by vertical bars which indicate the OD obtained by ELISA (Choo and Klug, (1997) Curr. Opin. Str. Biol. 7:117–125). The amino acid sequences (SEQ ID NOS.: 8, 62–64, 7 & 5) of the variant α-helical regions from the selected zinc fingers are: REDVLIRHGK (x) (SEQ ID NO.: 5), RADALMVHKR (y) (SEQ ID NO.: 6), and RGPDLARHGR (z) (SEQ ID NO.: 7). The DNA sequences (SEQ ID NOS.: 55, 44 & 56) contain the generic binding site GCGGNGGCG (SEQ ID NO.: 4), where the central (bold) nucleotide was either: uracil (U), thymine (T), cytosine (C), or 5-methylcytosine (M).
Figure 4A:
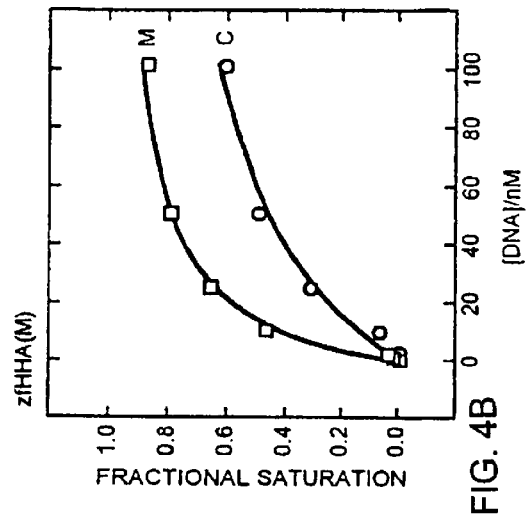
FIG. 4 is analogous to FIG. 2 and shows the binding curves for four of the polypeptides as described in FIG. 3 to their respective oligonucleotides.
Figure 4B:
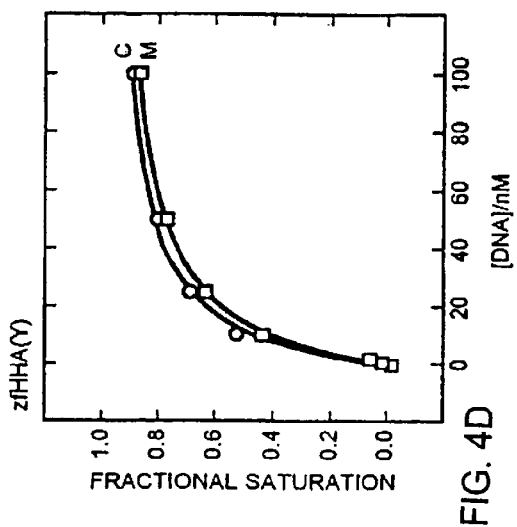
Figure 4C:
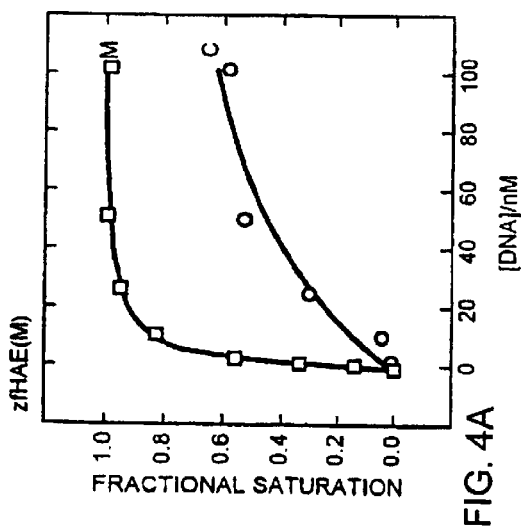
Figure 4D:
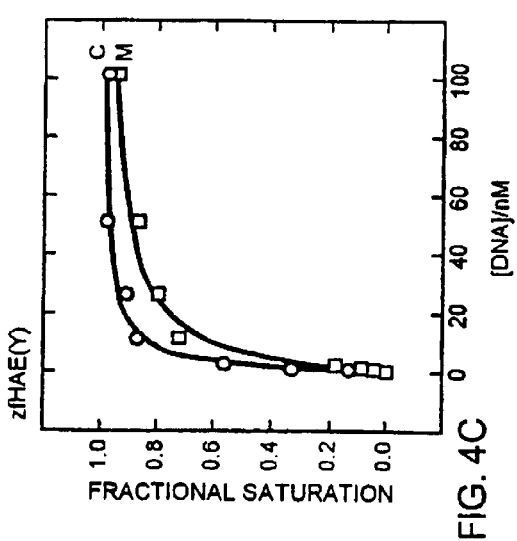

Randomization of zinc finger polypeptides may involve randomization at the DNA or protein level. Mutagenesis and screening of zinc finger polypeptides may be achieved by any suitable means. Preferably, the mutagenesis is performed at the nucleic acid level, for example by synthesizing novel genes encoding mutant proteins and expressing these to obtain a variety of different proteins. Alternatively, existing genes can be themselves mutated, such by site-directed or random mutagenesis, in order to obtain the desired mutant genes.

Mutations may be performed by any method known to those of skill in the art. Preferred, however, is site-directed mutagenesis of a nucleic acid sequence encoding the protein of interest. A number of methods for site-directed mutagenesis are known in the art, from methods employing single-stranded phage such as M13 to PCR-based techniques (see "PCR Protocols: A guide to methods and applications", M. A. Innis, D. H. Gelfand, J. J. Sninsky, T. J. White (eds.). Academic Press, New York, 1990). Preferably, the commercially available Altered Site II Mutagenesis System (Promega) may be employed, according to the directions given by the manufacturer.

Randomisation of the zinc finger binding motifs produced according to the invention is preferably directed to those residues where the code provided herein gives a choice of residues. For example, therefore, positions +1, +5 and +8 are advantageously randomised, whilst preferably avoiding hydrophobic amino acids; positions involved in binding to the nucleic acid, notably −1, +2, +3 and +6, may be randomised also, preferably within the choices provided by the rules of the present invention.

Screening of the proteins produced by mutant genes is preferably performed by expressing the genes and assaying the binding ability of the protein product. A simple and advantageously rapid method by which this may be accomplished is by phage display, in which the mutant polypeptides are expressed as fusion proteins with the coat proteins of filamentous bacteriophage, such as the minor coat protein pII of bacteriophage m13 or gene III of bacteriophage Fd, and displayed on the capsid of bacteriophage transformed with the mutant genes. The target nucleic acid sequence is used as a probe to bind directly to the protein on the phage surface and select the phage possessing advantageous mutants, by affinity purification. The phage are then amplified by passage through a bacterial host, and subjected to further rounds of selection and amplification in order to enrich the mutant pool for the desired phage and eventually isolate the preferred clone(s). Detailed methodology for phage display is known in the art and set forth, for example, in U.S. Pat. No. 5,223,409; Choo and Klug, (1995) Current Opinions in Biotechnology 6:431–436; Smith, (1985) Science 228:1315–1317; and McCafferty et al., (1990) Nature 348:552–554; all incorporated herein by reference. Vector systems and kits for phage display are available commercially, for example from Pharmacia.

Specific peptide ligands such as zinc finger polypeptides may moreover be selected for binding to targets by affinity selection using large libraries of peptides linked to the C terminus of the lac repressor LacI (Cull et al., (1992) Proc Natl Acad Sci USA, 89, 1865–9). When expressed in E. coli the repressor protein physically links the ligand to the encoding plasmid by binding to a lac operator sequence on the plasmid.

An entirely in vitro polysome display system has also been reported (Mattheakis et al., (1994) Proc Natl Acad Sci USA, 91, 9022–6) in which nascent peptides are physically attached via the ribosome to the RNA which encodes them.

The library of the invention may randomised at those positions for which choices are given in the rules of the first embodiment of the present invention. In particular, the members of the library are randomised at position +3 for binding to a central 5-meC residue. In such a case, 5-meC binding polypeptides will be selected by comparative binding analyses against methylated and non-methylated binding sites. However, the rules set forth above allow the person of ordinary skill in the art to make informed choices concerning the desired codon usage at the given positions. For instance, position +3 in the case of a central 5-meC residue should be Ala residue, encoded by the codon GCN.

Zinc finger binding motifs designed according to the invention may be combined into nucleic acid binding proteins having a multiplicity of zinc fingers. Preferably, the proteins have at least two zinc fingers. In nature, zinc finder binding proteins commonly have at least three zinc fingers, although two-zinc finger proteins such as Tramtrack are known. The presence of at least three zinc fingers is preferred. Binding proteins may be constructed by joining the required fingers end to end, N-terminus to C-terminus. Preferably, this is effected by joining together the relevant nucleic acid coding sequences encoding the zinc fingers to produce a composite coding sequence encoding the entire binding protein. The invention therefore provides a method for producing a DNA binding protein as defined above, wherein the DNA binding protein is constructed by recombinant DNA technology, the method comprising the steps of:

a) preparing a nucleic acid coding sequence encoding two or more zinc finger binding motifs as defined above, placed N-terminus to C-terminus;

b) inserting the nucleic acid sequence into a suitable expression vector; and c) expressing the nucleic acid sequence in a host organism in order to obtain the DNA binding protein.

A "leader" peptide may be added to the N-terminal finger. Preferably, the leader peptide is MAEEKP (SEQ ID NO.:39).

The nucleic acid encoding the DNA binding protein according to the invention can be incorporated into vectors for further manipulation. As used herein, vector (or plasmid) refers to discrete elements that are used to introduce heterologous nucleic acid into cells for either expression or replication thereof. Selection and use of such vehicles are well within the skill of the person of ordinary skill in the art. Many vectors are available, and selection of appropriate vector will depend on the intended use of the vector, i.e. whether it is to be used for DNA amplification or for nucleic acid expression, the size of the DNA to be inserted into the vector, and the host cell to be transformed with the vector. Each vector contains various components depending on its function (amplification of DNA or expression of DNA) and the host cell for which it is compatible. The vector components generally include, but are not limited to, one or more of the following an origin of replication, one or more marker genes, an enhancer element, a promoter, a transcription termination sequence and a signal sequence.

Both expression and cloning vectors generally contain nucleic acid sequence that enable the vector to replicate in one or more selected host cells. Typically in cloning vectors this sequence is one that enables the vector to replicate independently of the host chromosomal DNA, and includes origins of replication or autonomously replicating sequences. Such sequences are well known for a variety of bacteria, yeast and viruses. The origin of replication from the plasmid pBR322 is suitable for most Gram-negative bacteria, the 2μ plasmid origin is suitable for yeast, and various viral origins (e.g. SV 40, polyoma, adenovirus) are useful for cloning vectors in mammalian cells. Generally, the origin of replication component is not needed for mammalian expression vectors unless these are used in mammalian cells competent for high level DNA replication, such as COS cells.

Most expression vectors are shuttle vectors, i.e. they are capable of replication in at least one class of organisms but can be transfected into another class of organisms for expression. For example, a vector is cloned in E. coli and then the same vector is transfected into yeast or mammalian cells even though it is not capable of replicating independently of the host cell chromosome. DNA may also be replicated by insertion into the host genome. However, the recovery of genomic DNA encoding the DNA binding protein is more complex than that of exogenously replicated vector because restriction enzyme digestion is required to excise DNA binding protein DNA. DNA can be amplified by PCR and be directly transfected into the host cells without any replication component.

Advantageously, an expression and cloning vector may contain a selection gene also referred to as selectable marker. This gene encodes a protein necessary for the survival or growth of transformed host cells crown in a selective culture medium. Host cells not transformed with the vector containing the selection gene will not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available from complex media.

As to a selective gene marker appropriate for yeast, any marker gene can be used which facilitates the selection for transformants due to the phenotypic expression of the marker gene. Suitable markers for yeast are, for example, those conferring resistance to antibiotics G418, hygromycin or bleomycin, or provide for prototrophy in an auxotrophic yeast mutant, for example the URA3, LEU2, LYS2, TRP1, or HIS3 gene.

Since the replication of vectors is conveniently done in E. coli, an E. coli genetic marker and an E. coli origin of replication are advantageously included. These can be obtained from E. coli plasmids, such as pBR322, Bluescript© vector or a pUC plasmid, e.g. pUC18 or pUC19, which contain both E. coli replication origin and E. coli genetic marker conferring resistance to antibiotics, such as ampicillin.

Suitable selectable markers for mammalian cells are those that enable the identification of cells competent to take up DNA binding protein nucleic acid, such as dihydrofolate reductase (DHFR, methotrexate resistance), thymidine kinase, or genes conferring resistance to G418 or hygromycin. The mammalian cell transformants are placed under selection pressure which only those transformants which have taken up and are expressing the marker are uniquely adapted to survive. In the case of a DHFR or glutamine synthase (GS) marker, selection pressure can be imposed by culturing the transformants under conditions in which the pressure is progressively increased, thereby leading to amplification (at its chromosomal integration site) of both the selection gene and the linked DNA that encodes the DNA binding protein. Amplification is the process by which genes in greater demand for the production of a protein critical for growth, together with closely associated genes which may encode a desired protein, are reiterated in tandem within the chromosomes of recombinant cells. Increased quantities of desired protein are usually synthesised from thus amplified DNA.

Expression and cloning vectors usually contain a promoter that is recognised by the host organism and is operably linked to DNA binding protein encoding nucleic acid. Such a promoter may be inducible or constitutive. The promoters are operably linked to DNA encoding the DNA binding protein by removing the promoter from the source DNA by restriction enzyme digestion and inserting the isolated promoter sequence into the vector. Both the native DNA binding protein promoter sequence and many heterologous promoters may be used to direct amplification and/or expression of DNA binding protein encoding DNA.

Promoters suitable for use with prokaryotic hosts include, for example, the β-lactamase and lactose promoter systems, alkaline phosphatase, the tryptophan (trp) promoter system and hybrid promoters such as the tac promoter. Their nucleotide sequences have been published, thereby enabling the skilled worker operably to ligate them to DNA encoding DNA binding protein, using linkers or adapters to supply any required restriction sites. Promoters for use in bacterial systems will also generally contain a Shine-Delgarno sequence operably linked to the DNA encoding the DNA binding protein.

Preferred expression vectors are bacterial expression vectors which comprise a promoter of a bacteriophage such as phagex or T7 which is capable of functioning in the bacteria. In one of the most widely used expression systems, the nucleic acid encoding the fusion protein may be transcribed from the vector by T7 RNA polymerase (Studier et al, Methods in Enzymol. 185; 60–89, 1990). In the E. coli BL21(DE3) host strain, used in conjunction with pET vectors, the T7 RNA polymerase is produced from the λ-lysogen DE3 in the host bacterium, and its expression is under the control of the IPTG inducible lac UV5 promoter. This system has been employed successfully for overproduction of many proteins. Alternatively the polymerase gene may be introduced on a lambda phage by infection with an int-phage such as the CE6 phage which is commercially available (Novagen, Madison, USA), other vectors include vectors containing the lambda PL promoter such as PLEX (Invitrogen, NL), vectors containing the trc promoters such as pTrcHisXpress™ (Invitrogen) or pTrc99 (Pharmacia Biotech, SE) or vectors containing the tac promoter such as pKK223-3 (Pharmacia Biotech) or PMAL (New England Biolabs, MA. USA).

Moreover, the DNA binding protein gene according to the invention preferably includes a secretion sequence in order to facilitate secretion of the polypeptide from bacterial hosts, such that it will be produced as a soluble native-peptide rather than in an inclusion body. The peptide may be recovered from the bacterial periplasmic space, or the culture medium, as appropriate.

Suitable promoting sequences for use with yeast hosts may be regulated or constitutive and are preferably derived from a highly expressed yeast gene, especially a *Saccharomyces cerevisiae* gene. Thus, the promoter of the TRP1 gene, the ADHI, or ADHII gene, the acid phosphatase (PH05) gene, a promoter of the yeast mating pheromone genes coding for the a- or α-factor or a promoter derived from a gene encoding a glycolytic enzyme such as the promoter of the enolase, glyceraldehyde-3-phosphate dehydrogenase (GAP), 3-phospho glycerate kinase (PGK), hexokinase, pyruvate decarboxylase, phosphofructokinase, glucose-6-phosphate isomerase, 3-phosphoglycerate mutase, pyruvate kinase, triose phosphate isomerase, phosphoglucose isomerase or glucokinase genes, or a promoter from the TATA binding protein (TBP) gene can be used. Furthermore, it is possible to use hybrid promoters comprising upstream activation sequences (UAS) of one yeast gene and downstream promoter elements including a functional TATA box of another yeast gene, for example a hybrid promoter including the UAS(s) of the yeast PH05 gene and downstream promoter elements including a functional TATA box of the yeast GAP gene (PH05-GAP hybrid promoter). A suitable constitutive PH05 promoter is e.g. a shortened acid phosphatase PH05 promoter devoid of the upstream regulatory elements (UAS) such as the PH05 (−173) promoter element starting at nucleotide −173 and ending at nucleotide −9 of the PH05 gene.

DNA binding protein gene transcription from vectors in mammalian hosts may be controlled by promoters derived from the genomes of viruses such as polyoma virus, adenovirus, fowlpox virus, bovine papilloma virus, avian sarcoma virus, cytomegalovirus (CMV), a retrovirus and Simian Virus 40 (SV40), from heterologous mammalian promoters such as the actin promoter or a very strong promoter, e.g. a ribosomal protein promoter, and from the promoter normally associated with DNA binding protein sequence, provided such promoters are compatible with the host cell systems.

Transcription of a DNA encoding DNA binding protein by higher eukaryotes may be increased by inserting an enhancer sequence into the vector. Enhancers are relatively orientation and position independent. Many enhancer sequences are known from mammalian genes (e.g. elastase and globin). However, typically one will employ an enhancer from a eukaryotic cell virus. Examples include the SV40 enhancer on the late side of the replication origin (bp 100–270) and the CMV early promoter enhancer. The enhancer may be spliced into the vector at a position 5' or 3' to DNA binding protein DNA, but is preferably located at a site 5' from the promoter.

Advantageously, a eukaryotic expression vector encoding a DNA binding protein according to the invention may comprise a locus control region (LCR). LCRs are capable of directing high-level integration site independent expression of transgenes integrated into host cell chromatin, which is of importance especially where the DNA binding protein gene is to be expressed in the context of a permanently-transfected eukaryotic cell line in which chromosomal integration of the vector has occurred, or in transgenic animals.

Eukaryotic vectors may also contain sequences necessary for the termination of transcription and for stabilising the mRNA. Such sequences are commonly available from the 5' and 3' untranslated regions of eukaryotic or viral DNAs or cDNAs. These regions contain nucleotide segments transcribed as polyadenylated fragments in the untranslated portion of the mRNA encoding DNA binding protein.

An expression vector includes any vector capable of expressing DNA binding protein nucleic acids that are operatively linked with regulatory sequences, such as promoter regions, that are capable of expression of such DNAs. Thus, an expression vector refers to a recombinant DNA or RNA construct, such as a plasmid, a phage, recombinant virus or other vector, that upon introduction into an appropriate host cell, results in expression of the cloned DNA. Appropriate expression vectors are well known to those with ordinary skill in the art and include those that are replicable in eukaryotic and/or prokaryotic cells and those that remain episomal or those which integrate into the host cell genome. For example, DNAs encoding DNA binding protein may be inserted into a vector suitable for expression of cDNAs in mammalian cells, e.g. a CMV enhancer-based vector such as pEVRF (Matthias, et al., (1989) NAR 17, 6418).

Particularly useful for practising the present invention are expression vectors that provide for the transient expression of DNA encoding DNA binding protein in mammalian cells. Transient expression usually involves the use of an expression vector that is able to replicate efficiently in a host cell, such that the host cell accumulates many copies of the expression vector, and, in turn, synthesises high levels of DNA binding protein. For the purposes of the present invention, transient expression systems are useful e.g. for identifying DNA binding protein mutants, to identify potential phosphorylation sites, or to characterise functional domains of the protein.

Construction of vectors according to the invention employs conventional ligation techniques. Isolated plasmids or DNA fragments are cleaved, tailored, and religated in the form desired to generate the plasmids required. If desired, analysis to confirm correct sequences in the constructed plasmids is performed in a known fashion. Suitable methods for constructing expression vectors, preparing in vitro transcripts, introducing DNA into host cells, and performing analyses for assessing DNA binding protein expression and function are known to those skilled in the art. Gene presence, amplification and/or expression may be measured in a sample directly, for example, by conventional Southern blotting, Northern blotting to quantitate the transcription of mRNA, dot blotting (DNA or RNA analysis), or in situ hybridisation, using an appropriately labelled probe which may be based on a sequence provided herein. Those skilled in the art will readily envisage how these methods may be modified, if desired.

In accordance with another embodiment of the present invention, there are provided cells containing the above-described nucleic acids. Such host cells such as prokaryote, yeast and higher eukaryote cells may be used for replicating DNA and producing the DNA binding protein. Suitable prokaryotes include eubacteria, such as Gram-negative or Gram-positive organisms, such as *E. coli*, e.g. *E. coli* K-12 strains. DH5α and HB101, or *Bacilli*. Further hosts suitable for the DNA binding protein encoding vectors include eukaryotic microbes such as filamentous fungi or yeast. e.g. *Saccharomyces cerevisiae*. Higher eukaryotic cells include insect and vertebrate cells, particularly mammalian cells including human cells, or nucleated cells from other multicellular organisms. In recent years propagation of vertebrate cells in culture (tissue culture) has become a routine procedure. Examples of useful mammalian host cell lines are epithelial or fibroblastic cell lines such as Chinese hamster ovary (CHO) cells, NIH 3T3 cells, HeLa cells or 293T cells. The host cells referred to in this disclosure comprise cells in in vitro culture as well as cells that are within a host animal.

DNA may be stably incorporated into cells or may be transiently expressed using methods known in the art. Stably transfected mammalian cells may be prepared by transfecting cells with an expression vector having a selectable marker gene, and growing the transfected cells under conditions selective for cells expressing the marker gene. To prepare transient transfectants, mammalian cells are transfected with a reporter gene to monitor transfection efficiency.

To produce such stably or transiently transfected cells, the cells should be transfected with a sufficient amount of the DNA binding protein-encoding nucleic acid to form the DNA binding protein. The precise amounts of DNA encoding the DNA binding protein may be empirically determined and optimised for a particular cell and assay.

Host cells are transfected or, preferably, transformed with the above-captioned expression or cloning vectors of this invention and cultured in conventional nutrient media modified as appropriate for inducing promoters, selecting transformants, or amplifying the genes encoding the desired sequences. Heterologous DNA may be introduced into host cells by any method known in the art, such as transfection with a vector encoding a heterologous DNA by the calcium phosphate coprecipitation technique or by electroporation. Numerous methods of transfection are known to the skilled worker in the field. Successful transfection is generally recognised when any indication of the operation of this vector occurs in the host cell. Transformation is achieved using standard techniques appropriate to the particular host cells used.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g. Sambrook et al. (1989) Molecular Cloning: A Laboratory Manual, Second Edition, Cold Spring Harbor Laboratory Press).

Transfected or transformed cells are cultured using media and culturing methods known in the art, preferably under conditions, whereby the DNA binding protein encoded by the DNA is expressed. The composition of suitable media is known to those in the art, so that they can be readily prepared. Suitable culturing media are also commercially available.

DNA binding proteins according to the invention may be employed in a wide variety of applications, including diagnostics and as research tools. Advantageously, they may be employed as diagnostic tools for identifying the presence of modified nucleic acid molecules in a complex mixture. DNA binding molecules according to the invention can differentiate single base modifications in target DNA molecules.

For example, zinc fingers may be fused to nucleic acid cleavage moieties, such as the catalytic domain of a restriction enzyme, to produce a restriction enzyme capable of cleaving only methylated DNA (see Kim, et al., (1996) Proc. Natl. Acad. Sci. USA 93:1156–1160). Using such approaches, different zinc finger domains can be used to create restriction enzymes with any desired recognition nucleotide sequence, but which cleave DNA conditionally dependent on the particular modification of the nucleotides, for instance methylation of the cytosine ring at position 5.

5-meC targeting zinc fingers may moreover be employed in the regulation of gene transcription, for example by specific cleavage of methylated (or unmethylated) sequences using a fusion polypeptide comprising a zinc finger targeting domain and a DNA cleavage domain, or by fusion of an activating domain (such as HSV VP16) to a zinc finger, to activate transcription from a gene which possesses the zinc finger binding sequence in its upstream sequences. Activation only occurs when the target DNA is modified, such as by methylation. Zinc fingers capable of differentiating between U and T may be used to preferentially target RNA or DNA, as required. Where RNA-targeting polypeptides are intended, these are included in the term "DNA-binding molecule".

In a preferred embodiment, the zinc finger polypeptides of the invention may be employed to detect the presence of a particular base modification in a target nucleic acid sequence in a sample.

Accordingly, the invention provides a method for determining the presence of a target modified nucleic acid molecule, comprising the steps of:

a) preparing a DNA binding protein by the method set forth above which is specific for the target modified nucleic acid molecule;

b) exposing a test system comprising the target modified nucleic acid molecule to the DNA binding protein under conditions which promote binding, and removing any DNA binding protein which remains unbound;

c) detecting the presence of the DNA binding protein in the test system.

In a preferred embodiment, the DNA binding molecules of the invention can be incorporated into an ELISA assay. For example, phage displaying the molecules of the invention can be used to detect the presence of the target DNA, and visualised using enzyme-linked anti-phage antibodies.

Further improvements to the use of zinc finger phage for diagnosis can be made, for example, by co-expressing a marker protein fused to the minor coat protein (gVIII) of bacteriophage. Since detection with an anti-phage antibody would then be obsolete, the time and cost of each diagnosis would be further reduced. Depending on the requirements, suitable markers for display right include the fluorescent proteins (A. B. Cubitt, et al., (1995) Trends Biochem Sci. 20, 448–455; T. T. Yang. et al., (1996) Gene 173, 19–23), or an enzyme such as alkaline phosphatase which has been previously displayed on gIII (J. McCafferty, R. H. Jackson, D. J. Chiswell, (1991) Protein Engineering 4, 955–961) Labelling different types of diagnostic phase with distinct markers would allow multiplex screening of a single DNA sample. Nevertheless, even in the absence of such refinements, the basic ELISA technique is reliable, fast, simple and particularly inexpensive. Moreover it requires no specialised apparatus, nor does it employ hazardous reagents such as radioactive, isotopes, making it amenable to routine use in the clinic. The major advantage of the protocol is that it obviates the requirement for gel electrophoresis, and so opens the way to automated DNA diagnosis.

The invention provides DNA binding proteins which can be engineered with exquisite specificity. The invention lends itself, therefore, to the design of any molecule of which specific DNA binding is required. For example, the proteins according to the invention may be employed in the manufacture of chimeric restriction enzymes, in which a nucleic acid cleaving domain is fused to a DNA binding domain comprising a zinc finger as described herein.

The invention is described below, for the purpose of illustration only, in the following examples.

EXAMPLE 1

Preparation and Screening of a Zinc Finger Phage Display Library

A powerful method of selecting DNA binding proteins is the cloning of peptides (Smith (1985) Science 228, 1315–1317), or protein domains (McCafferty et al., (1990) Nature 348:552–554; Bass et al., (1990) Proteins 8:309–314), as fusions to the minor coat protein (pIII) of bacteriophage fd, which leads to their expression on the tip of the capsid. A phage display library is created comprising variants of the middle finger from the DNA binding domain of Zif268.

Materials and Methods

Construction And Cloning Of Genes. In general, procedures and materials are in accordance with guidance given in Sambrook et al., Molecular Cloning. A Laboratory Manual, Cold Spring Harbor, 1989. The gene for the Zif268 fingers (residues 333–420) is assembled from 8 overlapping synthetic oligonucleotides (see Choo and Klug, (1994) PNAS (USA) 91:11163–67), giving SfiI and NotI overhangs. The genes for fingers of the phage library are synthesised from 4 oligonucleotides by directional end to end ligation using 3 short complementary linkers, and amplified by PCR from the single strand using forward and backward primers which contain sites for NotI and SfiI respectively. Backward PCR primers in addition introduce Met-Ala-Glu as the first three amino acids of the zinc finger peptides, and these are followed by the residues of the wild type or library fingers as required. Cloning overhangs are produced by digestion with SfiI and NotI where necessary. Fragments are ligated to 1 µg similarly prepared Fd-Tet-SN vector. This is a derivative of fd-tet-DOG1 (Hoogenboom et al., (1991) Nucleic Acids Res. 19, 4133–4137) in which a section of the pelB leader and a restriction site for the enzyme SfiI (underlined) have been added by site-directed mutagenesis using the oligonucleotide:

5'ctcctgcagt tggacctgtg ccatggccgg ctggccgca tagaatggaa caactaaagc 3' (SEQ ID NO.:11).

which anneals in the region of the polylinker. Electrocompetent DH5α cells are transformed with recombinant vector in 200 ng aliquots, grown for 1 hour in 2×TY medium with 1% glucose, and plated on TYE containing 15 µg/ml tetracycline and 1% glucose.

FIG. 1 shows the amino acid sequences of the three zinc fingers derived from Zif268 used in the phage display library of the present invention. The top and bottom rows represent the sequence of the first and third fingers respectively. The middle row represents the sequence of the middle finger. The randomised positions in the α-helix of the middle finger have residues marked 'X'. The amino acid positions are numbered relative to the first helical residue (position 1). For amino acids at positions −1 to +8, excluding the conserved Leu and His, codons are equal mixtures of (G,A,C)NN: T in the first base position is omitted in order to avoid stop codons, but this has the unfortunate effect that the codons for Trp, Phe, Tyr and Cys are not represented. Position +9 is specified by the codon A(G,A)G, allowing either Arg or Lys. Residues of the hydrophobic core are circled, whereas the zinc ligands are written as white letters on black circles. The positions forming the β-sheets and the α-helix of the zinc fingers are marked below the sequence.

Phage Selection. Colonies are transferred from plates to 200 ml 2×TY/Zn/Tet (2×TY containing 50 µM Zn(CH$_3$COO)$_2$ and 15 µg/ml tetracycline) and grown overnight. Phage are purified from the culture supernatant by two rounds of precipitation using 0.2 volumes of 20% PEG/2.5M NaCl containing 50 µM Zn(CH3.COO)$_2$, and resuspended in zinc finger phage buffer (20 mM HEPES pH7.5, 50 mM NaCl, 1 mM MgCl$_2$ and 50 µM Zn(CH3.COO)$_2$). Streptavidin-coated paramagnetic beads (Dynal) are washed in zinc finger phage buffer and blocked for 1 hour at room temperature with the same buffer made up to 6% in fat-free dried milk (Marvel). Selection of phage is over three rounds: in the first round, beads (1 mg) are saturated with biotinylated oligonucleotide (~80 nM) and then washed prior to phage binding, but in the second and third rounds 1.7 nM oligonucleotide and 5 µg poly dGC (Sigma) are added to the beads with the phage. Binding reactions (1.5 ml) for 1 hour at 15° C. are in zinc finger phase buffer made up to 2% in fat-free dried milk (Marvel) and 1% in Tween 20, and typically contained 5×10$^{11}$ phage. Beads are washed 15 times with 1 ml of the same buffer. Phage are eluted by shaking in 0.1M triethylamine for 5 min and neutralised with an equal volume of 1M Tris pH7.4. Log phase E. coli TG1 in 2×TY are infected with eluted phage for 30 min at 37° C. and plated as described above. Phage titres are determined by plating serial dilutions of the infected bacteria.

Sequencing Of Selected Phage. Single colonies of transformants obtained after three rounds of selection as described, are grown overnight in 2×TY/Zn/Tet. Small aliquots of the cultures are stored in 15% glycerol at −20° C., to be used as an archive. Single-stranded DNA is prepared from phage in the culture supernatant and sequenced using the Sequenase™ 2.0 kit (U.S. Biochemical Corp.).

EXAMPLE 2

Isolation of Zinc Fingers Capable of C-T Differentiation

The phage are selected against oligonucleotides comprising the sequences GCGGCGGCG and GCGGTGGCG, some zinc finger DNA-binding domains are selected which bound both sequences equally well (FIG. 1b, c). However, two additional zinc finger families are isolated which are capable of differential binding to the two closely related sites (FIG. 1b, c). Sequence-specific recognition requires discrimination of the central base in the binding site by amino acids in position 3 of the recognition helix of the selected zinc fingers, and it is noted that aspartate is selected to bind opposite cytosine in the triplet GCG, while alanine is selected opposite thymine in the triplet GTG. The correlation between thymine and alanine is particularly significant, as it implies a van der Waals interaction between the amino acid side-chain and the 5-methyl group of the base. Indeed, when thymine is mutated to deoxyuracil in the binding sites of such fingers there is a dramatic decrease in the strength of the intermolecular interaction (FIG. 1c). This shows that these zinc fingers are capable of specifically recognising a 5-methyl group, and suggests that similar fingers might be selected which bind 5-meC by the same token.

EXAMPLE 3

Selection of 5-methylcytosine-specific zinc fingers

The phage display library is screened with the synthetic binding site GCGGMGGCG, containing a 5-meC base analogue (M). After 5 rounds of selection, zinc finger phage are tested for binding to 5-meC and cytosine in the context of the above site, and those capable of specifically binding the methylated site are sequenced in the region of the zinc finger gene. Two different clones are isolated, which are identical to the DNA-binding domains previously selected using the binding site (SEQ ID NO.: 44) GCGGTGGCG.

Hence the various zinc finger phage selections described above yield different fingers able to bind the generic DNA sequence (SEQ ID NO.: 4) GCGGNGGCG, where N is either thymine, cytosine or 5-meC. A full complement of fingers is selected for recognition of the cytosine/5-meC pair in the above context, some of which recognize one type of base exclusively, while others bound both bases equally well (FIGS. 1c and 2).

The zinc finger amino acid residues which are selected by the interaction between the randomised recognition helix and the central base of the DNA binding site are rationalised in terms of previously elucidated zinc finger-DNA recognition rules. Fingers with alanine in position +3 of the recognition helix specifically bind 5-meC and thymine owing to a tight hydrophobic interaction between the side chain and the 5-methyl group which is present in both bases. In contrast, a finger with valine in position +3 is also able to accommodate cytosine in addition to the two methylated bases, by the use of different rotamers. Fingers with aspartate in position +3 bind cytosine specifically, for example by forming a ring structure which packs against the pyrimidine as is observed in the refined crystal structure of Zif268.

EXAMPLE 4

Selection of 5-meC Specific Zinc Fingers Using Cross-Strand Specificity

1. General Procedures

Construction of Overlapping Finger Phage Display Libraries

Two zinc finger DNA binding domain libraries are constructed comprising the amino acid framework of wild-type Zif268, but containing randomisations in amino acid positions of fingers 2 and 3. The first library contains randomisations at F2 residue position 6 and F3 residue positions −1, 1, 2 and 3 and recognises sequences of the form 5'-GXX-XCG-GCG-3'. The second library additionally contains variations in F2 position 3 and F3 positions 5 and 6 and recognises sequences of the form 5'-XXX-XXG-GCG-3'. The libraries are denoted collectively as LF-2/3.

The genes for the two zinc finger phage display libraries are assembled from synthetic DNA oligonucleotides by directional end-to-end ligation using short complements DNA linkers. The oligonucleotides contain selectively randomised codons, encoding all 20 amino acids or a subset thereof, in the appropriate amino acid positions of fingers 2 and 3. The constructs are amplified by PCR using primers containing Not I and Sfi I restriction sites, digested with the above endonucleases to produce cloning overhangs, and ligated into vector Fd-Tet-SN. Electrocompetent E. coli TG1 cells are transformed with the recombinant vector and plated onto TYE medium (1.5% (w/v) agar, 1% (w/v) Bactotryptone, 0.5% (w/v) Bacto yeast extract, 0.8% (w/v) NaCl) containing 15 mg/ml tetracycline.

Phage Selections

Tetracycline resistant colonies are transferred from plates into 2×TY medium (16 g/liter Bactotryptone, 10 g/liter Bacto yeast extract, 5 g/liter NaCl) containing 50 µM ZnCl$_2$ and 15 µg/ml tetracycline, and cultured overnight at 30° C. in a shaking incubator. Cleared culture supernatant containing phage particles is obtained by centrifuging at 300 g for 5 minutes.

DNAs of the form 5'-tatagtg-xxxx-ggcgtgtcacagtcagtccacacacgtc-3' (SEQ. ID NO.:12), and their complementary strands, are chemically synthesized and annealed in 20 mM Tris-HCl, pH 8, 100 mM NaCl. The DNA sequences-XXXX-represent nucleotide sequences after methylation by M. HaeIII (GGMC) or M. HhaI (GMGC). Since DNA is chemically synthesized, the DNA sites used in selections incorporate 5-meC (in appropriate positions on both strands) with 100% yield. Selections are also carried out on derivatives of these sites containing thymine rather than 5-meC in the appropriate positions (and with A rather than C on the complementary strand as appropriate).

One picomole of each target site is bound to streptavidin-coated tubes (Boehringer Mannheim) in 50 µl PBS containing 50 µM ZnCl$_2$. Bacterial culture supernatant containing phage is diluted 1:10 in selection buffer (PBS containing 50 µM ZnCl$_2$, 2% (w/v) fat-free dried milk (Marvel), 1% (v/v) Tween, 20 µg/ml sonicated salmon sperm DNA), and 1 ml is applied to each tube. In order to increase the selection pressure. 50 pmol soluble (unbiotinylated) competitor sites are synthesised and added to the binding mixtures: selections for phage that bind the methylated DNA contain competitors with cytosine or thymine at the appropriate positions: selections for phage that discriminate thymine instead of 5-meC in the recognition sites of the methylase enzymes contain DNA competitors with cytosine or 5-meC at the appropriate positions. After 1 hour at 20° C., the tubes are emptied and washed 20 times with PBS containing 50 µM ZnCl$_2$, 2% (w/v) fat-free dried milk (Marvel) and 1% (v/v) Tween. Retained phage are eluted in 0.1 ml 0.1M triethylamine and neutralised with an equal volume of 1M Tris (pH 7.4). Logarithmic-phase E. coli TG1 (0.5 ml) are infected with eluted phage (50 ml), and cultured overnight at 30° C. in 2×TY medium containing 50 µM ZnCl$_2$ and 15 µg/ml tetracycline, to prepare phage for subsequent rounds of selection. After 4 rounds of selection, E. coli TG1 infected with selected phage are plated, individual colonies are picked and used to prepare phase for ELISA assays and DNA sequencing.

ELISA to Determine Nucleotide Discrimination.

Binding sites are synthesised as described above, including biotinylated sites where 5-meC (M) is replaced by a C or T (with appropriate bases in the complementary strand). Two-fold dilutions of DNA are added to separate wells of a streptavidin-coated microtitre plate (Boehringer Mannheim) in 50 µl PBS containing 50 µM ZnCl$_2$ (PBS/Zn). Phage solution (bacterial culture supernatant diluted 1:10 in PBS/Zn containing 2% (w/v) fat-free dried milk (Marvel), 1% (v/v) Tween and 20 µg/ml sonicated salmon sperm DNA) are applied to each well (50 µl/well). Binding is allowed to proceed for one hour at 20° C. Unbound phage are removed by washing 6 times with PBS/Zn containing 1% (v/v) Tween, then 3 times with PBS/Zn. Bound phage are detected by ELISA using horseradish peroxidase-conjugated anti-M13 IgG (Pharmacia Biotech) and the colourimetric signal quantitated using SOFTMAX 2.32 (Molecular Devices).

ELISA Using an Enzymatically Methylated DNA Binding Site.

Complementary DNA oligonucleotides containing the sequences methylated by M.HaeIII and M.HhaI are chemically synthesised and annealed as described above. The DNA is used in binding assays without exposure to the methylases, or after reaction with either or both methylase enzymes according to the manufacturer's instructions (New England Biolabs). DNA binding sites (0.5 pmol) are added to wells of a streptavidin-coated microtitre plate (Boehringer Mannheim) in 50 µl PBS containing 50 µM ZnCl$_2$ (PBS/Zn). The binding of various zinc finger phage clones is assayed by ELISA as described above.

DNA Sequence Analysis

The coding sequence of individual zinc finger clones is amplified by PCR using external primers complementary to phage sequence. These PCR products are then sequenced manually using Thermo Sequenase cycle sequencing (Amersham Life Science).

2. Experimental Results

Design of Sequence-specific Zinc Finger Proteins which Bind Enzymatically Methylated DNA Sites.

The three-finger DNA-binding domain of transcription factor Zif268 binds the DNA sequence (SEQ ID NO.: 45)

GCGTGGGCG. Phage display libraries of this zinc finger domain have been used to elucidate aspects of the base-recognition mechanism of zinc fingers and to select fingers which bind to predetermined DNA sequences. We have constructed a set of phage display libraries in which amino acid positions from both finger 2 (F2) and finger 3 (F3) of Zif268 are simultaneously randomized in order to evaluate the effect of inter-finger synergy on the specificity of DNA binding. These libraries, hereafter denoted collectively as LF2/3, contain variants which specifically recognized DNA sequences of the form XXXXCGGCG or GXXXCGGCG, where X is any nucleotide.

The HaeIII and HhaI methyltransferases modify the internal cytosine (shown in bold lettering) of their respective DNA recognition sequences GGCC and GCGC. We therefore designed two DNA oligos, one containing the sequence (SEQ ID NO.: 13) GGCCCGGCG and the other (SEQ ID NO.: 14) GCGCCGGCG, which included the sites required for modification by the respective methylases M.HaeIII or M.HhaI (underlined). The oligos also place these sequences in the context of binding sites that could be used to screen LF2/3 for zinc fingers that specifically recognize the modified DNA The two different target DNA oligonucleotides are prepared using solid phase DNA synthesis such that 5-meC is be chemically incorporated into the appropriate positions (shown in bold lettering) with 100% yield, and a biotin group is added to the 5' terminus of one DNA strand. The synthetically modified DNAs are coupled to a solid support coated with streptavidin and used in separate phage selections as described above. After four rounds of selection, individual zinc finger clones from either selection are screened by phage ELISA for binding to the methylated form of their DNA target site and discrimination against a control oligo containing the unmodified DNA. Four different zinc finger phage clones with varying specificity are selected for further study: (i) clone zfHAE(M) preferentially binds the methylated DNA incorporating the HaeIII site; (ii) clone zfHHA(M) preferentially binds the methylated DNA incorporating the HhaI site; (iii) clone zfHAE(Y) binds the DNA incorporating the HaeIII site regardless of the methylation status; and (iv) clone zfHHA(Y) binds the DNA incorporating the HhaI site regardless of the methylation status.

Table 1 shows the sequences of the oligonucleotides used for selection and of the resulting clones obtained.

TABLE 1

Oligonucleotide Sequeuces

| | | |
|---|---|---|
| HAE(M) | 5'-tatagtG-GGMC-GGCGtgtcacagtcagtccacacacgtc-3' | (SEQ ID NO.: 15) |
| HHA(M) | 5'-tatagtG-GMGC-GGCGtgtcacagtcagtccacacacgtc-3' | (SEQ ID NO.: 16) |
| HAE(Y) | 5'-tatagtG-GGYC-GGCGtgtcacagtcagtccacacacgtc-3' | (SEQ ID NO.: 17) |
| HHA(Y) | 5'-tatagtG-GYGC-GGCGtgtcacagtcagtccacacacgtc-3' | (SEQ ID NO.: 18) |
| HAE(T) | 5'-tatagtG-GGTC-GGCGtgtcacagtcagtccacacacgtc-3' | (SEQ ID NO.: 19) | wherein: M = 5-me
Y = pyrimidine (C/T/M)
R = Purine (A/G)

Zinc Finger Clones

| | F1<br>-1 1 2 3 4 5 6 | F2<br>-1 1 2 3 4 5 6 | F3<br>-1 1 2 3 4 5 6 |
|---|---|---|---|
| zfHAE(M) | R S D E L T R<br>(SEQ ID NO.:20) | R S D D L S Q<br>(SEQ ID NO.:25) | R K H H R K E<br>(SEQ ID NO.:30) |
| zfHHA(M) | R S D E L T R<br>(SEQ ID NO.:21) | R S D D L T R<br>(SEQ ID NO.:26) | Y D G A R K R<br>(SEQ ID NO.:31) |
| zfHAE(Y) | R S D E L T R<br>(SEQ ID NO.:22) | R S D D L T G<br>(SEQ ID NO.:27) | H N R D R K R<br>(SEQ ID NO.:32) |
| zfHHA(Y) | R S D E L T R<br>(SEQ ID NO.:23) | R S D H L S A<br>(SEQ ID NO.:28) | T N S T R T K<br>(SEQ ID NO.:33) |
| zfHAE(T) | R S D E L T R<br>(SEQ ID NO.:24) | R S D D L S T<br>(SEQ ID NO.:29) | R N D H R K T<br>(SEQ ID NO.:34) |

Figure 5C:
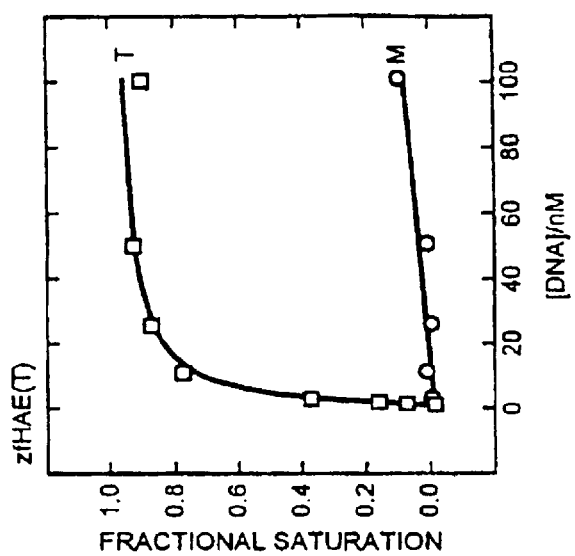
FIG. 5 shows discrimination between 5-meC and T by zfHAE(M).
Figure 5B:
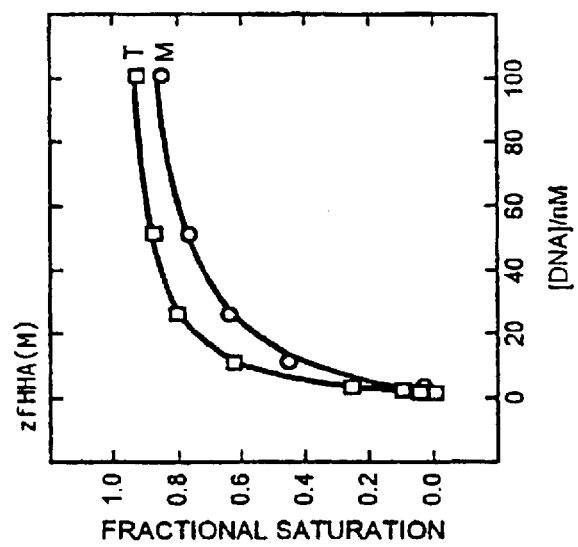
Figure 5A:
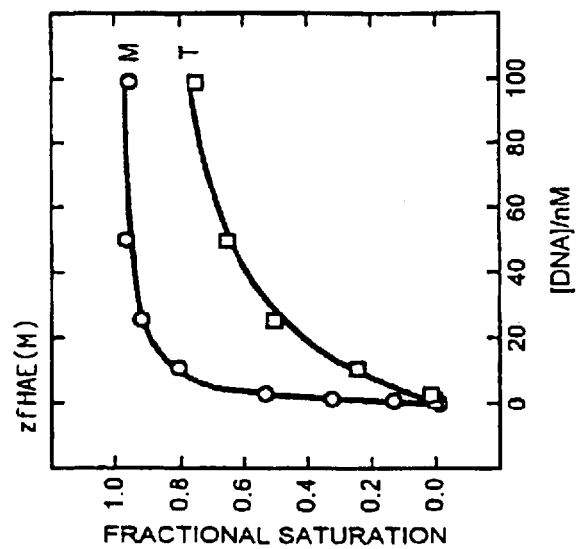

Zinc finger phage binding for each of the above clones is titrated against different amounts of methylated and unmethylated DNA oligos to derive values of the apparent dissociation constants ($K_d$s) for either DNA binding site (see FIGS. 4 and 5). The apparent Kd of each clone for the optimally bound DNA site(s) is in the nanomolar range, similar to that of wild-type Zif268 DNA-binding domain for its preferred target site using this assay. The $K_d$s obtained are shown in Table 2. Clones zfHAE(M) (Table 1 F1: SEQ ID NO.:20; F2: SEQ ID NO.:25; F3: SEQ ID NO.:30) and zfHHA(M) (Table 1 F1: SEQ ID NO.:21; F2: SEQ ID NO.:26; F3: SEQ ID NO.:31) preferentially bind their respective DNA target sites when 5-meC is incorporated into the correct nucleotide positions, and discriminated against the unmethylated DNA sites by factors of approximately 20-fold and 5-fold, respectively. The discrimination shown by zfHAE(M) in particular is good considering the simple DNA recognition mechanism of zinc fingers, and that only a single functional group per DNA molecule has been altered Clones zfHAE(Y) (Table 1 F1: SEQ ID NO.:23; F2: SEQ ID NO.:27; F3: SEQ ID NO.:32) and zfHHA(Y) (Table 1 F1: SEQ ID NO.:24; F2: SEQ ID NO.:28; F3: SEQ ID NO.:33) bind their respective target sites but do not show any preference for either the modified or unmodified forms.

The four zinc finger clones isolated by phage display using synthetic 5-meC-containing DNA target sites are next tested for binding to enzymatically methylated DNA. In this assay a single DNA fragment is used that incorporates both the (SEQ ID NO.: 13) GGCCGGCG and the (SEQ ID NO. 14) GCGCCGGCG zinc finger binding site sequences (FIG. 6a), which additionally are substrates for methylation by M. HaeIII and M. HhaI respectively. Each zinc finger clone is tested for binding to the DNA before and after DNA modification using one or both methylases. FIG. 6b shows that, in contrast to zfHAE(Y) and zfHHA(Y) which both recognize the DNA regardless of the methylation status (as would be expected), zfHAE(M) and zfHHA(M) bind only after specific methylation of the DNA by the appropriate methylase enzyme. Thus enzymatic modification of cytosine to 5-meC can act as a switch that induces specific protein-DNA complex formation.

TABLE 2

K$_d$s of each clone for target and non-target oligonucleotides

| Clone | Oligonucleotide | K$_d$ |
|---|---|---|
| zfHAE(M) | G-GGMC-GGCG | 2.0 +/- 0.2 nM |
|  | G-GGCC-GGCG | 62 +/- 29 nM |
| zfHHA(M) | G-GMGC-GGCG | 14 +/- 3.2 nM |
|  | G-GCGC-GGCG | 62 +/- 22 nM |
| zfHAE(Y) | G-GGMC-GGCG | 6.3 +/- 1.4 nM |
|  | G-GGCC-GGCG | 2.0 +/- 0.2 nM |
| zfHHA(Y) | G-GMGC-GGCG | 14 +/- 2.0 nM |
|  | G-GCGC-GGCG | 11 +/- 2.4 nM |

In Table 2, clone zfHAE(M) sequences are represented by SEQ ID NOS.: 35–36, respectively, in order of appearance; clone zfHHA(M) sequences are represented by SEQ ID NOS.: 37–38, respectively, in order of appearance; clone zfHAE(Y) sequences are represented by SEQ ID NOS.: 46–47, respectively, in order of appearance; and clone zfHHA(Y) sequences are represented by SEQ ID NOS.: 48–49, respectively, in order of appearance.

Synergistic Zinc Finger Pairs that Discriminate 5-methylcytosine from Thymine.

The 5-methyl group of methylcytosine and thymine is a prominent feature of the DNA major groove which contributes important intermolecular (hydrophobic) contacts in protein-DNA interactions but is stereochemically indistinguishable in the two different bases. Consequently, zinc fingers—which frequently achieve DNA recognition by 1:1 contacts between amino acids and bases—often fail to discriminate between the two closely related bases. The phage-selected clone zfHHA(M) is one such zinc finger protein which accepts both thymine and 5-meC with almost equal affinity (FIG. 5). In this case it is likely that the aromatic ring of tyrosine forms equally good hydrophobic contacts with the methyl group of either base.

One way in which zinc finger proteins could distinguish 5-meC from thymine is to discriminate the complementary nucleotide in the base-pair. Zinc finger proteins such as Zif268 make base contacts predominantly to only one DNA strand—the 'antiparallel' strand—but, importantly, they can also form 'cross-strand' contacts to certain bases on the complementary, 'parallel' strand. It has been shown that these contacts can make important contributions to DNA-binding specificity, Thus the zinc fingers of Zif268 and related proteins can be regarded as binding to overlapping 4 bp subsites, where the specificity for the base-pair at the boundary between adjacent subsites potentially arises via contacts from two synergistic zinc fingers to each of the nucleotides in the base-pair (FIG. 3). Therefore a zinc finger protein can distinguish a 5-meC:G base-pair from a T:A base-pair provided they are positioned at the overlap between adjacent DNA subsites, such that a contact to the 'parallel' strand can be made.

This is the case for the DNA binding site (SEQ ID NO.: 50) GGMCCGGCG in which the 5-meC base (bold) is discriminated from thymine by zinc finger clone zfHAE(M). According to the conventional model of zinc finger-DNA recognition, based on the crystal structure of the Zif268-DNA complex and subsequent biochemical experiments, the 5-meC base in the binding site is contacted by the glutamine residue in α-helical position +6 of finger 2 (FIG. 3). Additionally, the complementary guanine can be recognized using a synergistic contact from the histidine residue in α-helical position +2 of finger 3 (FIG. 3).

In order to investigate further the discrimination between 5-meC and thymine, another zinc finger clone is selected, zfHAE(T), which is specific for thymine instead of 5-meC in the context of the above binding site. This clone makes use of a cross-strand contact from aspartate in position +2 of finger 3 to recognise adenine in the 'parallel' strand. In this respect zfHAE(T) is remarkably like the wild-type Zif268 DNA-binding domain, whose zinc fingers each have an Arg-Ser-Asp triad that makes inter- and intra-molecular contacts including cross-strand contacts from the aspartate. Discrimination in favour of thymine by zfHAE(T) is relatively stronger than discrimination for 5-meC by zfHAE(M), presumably owing to the stabilising effect of intramolecular (protein-protein buttressing) interactions and the favourable geometry of this network of contacts.

The dissociation constants for the interaction seen between zfHAE(M), zfHHA(M) and zfHAE(T) (Table 1 F1: SEQ ID NO.:24; F2: SEQ ID NO.:29; F3: SEQ ID NO.:34) and 5-meC or T oligonucleotides are set forth in Table 3.

TABLE 3

K$_d$s or each clone for 5-mcC and T oligonucleotides

| Clone | Oligonucleotide | K$_d$ |
|---|---|---|
| zfHAE(M) | G-GGMC-GGCG | 2.0 +/- 0.2 nM |
|  | G-GGTC-GGCG | 27 +/- 4.4 nM |
| zfHHA(M) | G-GMGC-GGCG | 14 +/- 3.2 nM |
|  | G-GTGC-GGCG | 6.1 +/- 4.5 nM |
| zfHAE(T) | G-GGMC-GGCG | 3.4 +/- 0.5 nM |
|  | G-GGTC-GGCG | n/a |

Clone zfHAE(M) sequences are represented by SEQ ID NOS.: 35 and 51, respectively, in order of appearance; clone zfHHA(M) sequences are represented by SEQ ID NOS.: 37 and 52, respectively, in order of appearance; and clone zfHAE(Y) sequences are represented by SEQ ID NOS.: 53–54, respectively, in order of appearance.

EXAMPLE 5

Methylcytosine-specific Restriction Enzyme

Phage-selected or rationally designed zinc finger domains which recognise modified bases, including 5-meC, can be converted to restriction enzymes which cleave DNA containing those modified bases, including 5-meC. This is achieved by coupling a modified base-specific zinc finger to a cleavage domain of a restriction enzyme or other nucleic acid cleaving moiety.

A method of converting zinc finger DNA-binding domains to chimaeric restriction endonucleases has been described in Kim, et al., (1996) Proc. Natl. Acad. Sci. USA 93:1156–1160. In order to demonstrate the applicability of methylcytosine-specific zinc fingers to restriction enzymes, a fusion is made between the catalytic domain of Fok I as described by Kim et al. and the 5-meC specific zinc finger described in Example 3. Fusions of the 5-meC zinc finger nucleic acid-binding domain to the catalytic domain of Fok I restriction enzyme results in a novel endonuclease which cleaves DNA adjacent to the DNA recognition sequence of the zinc finger, namely (SEQ ID NO.: 55) GCGGMGGCG.

The oligonucleotides (SEQ ID NO.: 55) GCGGMGGCG and (SEQ ID NO.: 43) GCGGCGGCG are synthesized and ligated to random DNA sequences. After incubation with the zinc finger restriction enzyme, the nucleic acids are analyzed by gel electrophoresis. Bands indicating cleavage of the nucleic acid at a position corresponding to the location of the oligonucleotide (SEQ ID NO.: 55) GCGGMGGCG are visible with the methylated, but not the unmethylated, nucleic acid.

In a further experiment, the 5-meC-specific zinc finger is fused to an amino terminal copper/nickel binding motif. Under the correct redox conditions (Nagaoka, M., et al., (1994) J. Am. Chem. Soc. 116:4085–4086), sequence-specific DNA cleavage is observed, only in the presence of 5-meC containing DNA incorporating the oligonucleotide (SEQ ID NO.: 55) GCGGMGGCG.

EXAMPLE 6

Determination of Methylase Activity in vivo

A reporter systems is produced which produces a reporter signal conditionally depending on the activity of a DNA methylase.

A transient transfection system using zinc finger transcription factors is produced as described in Choo, Y., et al., (1997) J. Mol. Biol 273:525–532. This system comprises an expression plasmid which produces a 5-meC specific phage-selected zinc finger fused to the activation domain of HSV VP16, and a reporter plasmid which contain the recognition sequence of the zinc finger upstream of a CAT reporter gene.

Thus, a zinc finger which recognises the DNA sequence (SEQ ID NO.:56) GCGGCCGCG selected by phage display as described in Choo, Y. & Klug, A. (1994) Proc. Natl. Acad, Sci. U.S.A. 91:11163–11167, by the method of the preceding examples, a further zinc finger is selected which is capable of binding to the sequences (SEQ ID NO.: 57) GCGGM-CGCG where the central base M is 5-meC, and used to construct transcription factors as described in the foregoing.

A transient expression experiment is conducted, wherein the CAT reporter gene on the reporter plasmid is placed downstream of the sequence (SEQ ID NO.: 56) GCGGC-CGCG. The reporter plasmid is cotransfected with a plasmid vector expressing the zinc finger-HSV fusion under the control of a constitutive promoter. No activation of CAT gene expression is observed.

However, when the same experiment is conducted in the presence of Hae III methylase, CAT expression is observed as a result of the methylation of (SEQ ID NO.: 56) GCG-GCCGCG to form (SEQ ID NO.: 58) GCGGMCGCG, and consequent binding of the zinc finger transcription factor to its recognition sequence.

What is claimed is:

1. A method for binding a DNA binding polypeptide of the Cys2 His2 zinc finger class to a DNA triplet in a target DNA sequence comprising 5-meC as the central residue in the target DNA triplet, the method comprising preparing a DNA binding polypeptide of the Cys2 His2 zinc finger class to bind to the DNA triplet, wherein binding to the 5-meC residue by an α-helical zinc finger DNA binding motif of the polypeptide is achieved by placing an Ala residue at position +3 of the α-helix of the zinc finger, and exposing the DNA binding polypeptide to the target DNA sequence, whereby the DNA binding polypeptide binds to the target DNA sequence.

2. A method for binding a DNA binding polypeptide of the Cys2 His2 zinc finger class to a DNA triplet in target DNA sequence comprising 5-meC, but not to an identical triplet comprising unmethylated C, the method comprising preparing a DNA binding polypeptide of the Cys2 His2 zinc finger class to bind to the triplet comprising 5-meC, wherein binding to each base of the triplet by an α-helical zinc finger DNA binding motif in the polypeptide is determined as follows:

a) if the 5' base in the triplet is G, then position +6 in the α-helix is Arg or position ++2 is Asp, or position +6 in the α-helix is Arg and position ++2 is Asp;

b) if the 5' base in the triplet is A, then position +6 in the α-helix is Gln or Glu and ++2 is not Asp;

c) if the 5' base in the triplet is T, then position +6 in the α-helix is Ser or Thr and position ++2 is Asp; or position +6 is a hydrophobic amino acid other than Ala;

d) if the 5' base in the triplet is C, then position +6 in the α-helix is any amino acid, provided that position ++2 in the α-helix is not Asp;

e) position +3 in the α-helix is Ala;

f) if the 3' base in the triplet is G, then position −1 in the α-helix is Arg;

g) if the 3' base in the triplet is A, then position −1 in the α-helix is Gln and position +2 is Ala;

h) if the 3' base in the triplet is T, then position −1 in the α-helix is Asn; or position −1 is Gln and position +2 is Ser;

i) if the 3' base in the triplet is C, then position −1 in the α-helix is Asp and Position +1 is Arg; and exposing the DNA binding polypeptide to the target DNA sequence, whereby the DNA binding polypeptide binds to the target DNA sequence.

3. The method according to claim 1 or 2, wherein the binding protein comprises two or more zinc finger binding motifs.

4. The method according to claim 3, wherein the DNA binding protein is constructed by recombinant DNA technology, the method comprising the steps of:

a) preparing a DNA coding sequence encoding two or more zinc finger binding motifs;

b) inserting the DNA sequence into a suitable expression vector; and
c) expressing the DNA sequence in a host organism in order to obtain the DNA binding protein.

5. The method according to claim 1 or 2 further comprising the steps of subjecting the DNA binding protein to one or more rounds of randomization and screening in order to improve the binding characteristics thereof.

6. The method of either of claims 1 or 2, further comprising detecting the DNA binding polypeptide binding to the target DNA sequence.

7. The method of either of claims 1 or 2, wherein the binding of the DNA binding polypeptide to the target DNA sequence regulates transcription of a gene.

\* \* \* \* \*

UNITED STATES PATENT AND TRADEMARK OFFICE
CERTIFICATE OF CORRECTION

PATENT NO. : 6,977,154 B1  Page 1 of 1
DATED : December 20, 2005
INVENTOR(S) : Yen Choo It is certified that error appears in the above-identified patent and that said Letters Patent is hereby corrected as shown below:

<u>Title page,</u>
Item [75], should read:
-- [75] Inventors: Yen Choo, Cambridge (GB) --.

Signed and Sealed this

Eleventh Day of April, 2006

JON W. DUDAS
*Director of the United States Patent and Trademark Office*

SEQUENCE LISTING

```
<160> NUMBER OF SEQ ID NOS: 81

<210> SEQ ID NO 1
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Tyr Lys Cys Pro Glu Cys Gly Lys Ser Phe Ser Gln Lys Ser Asp
 1               5                  10                  15

Leu Val Lys His Gln Arg Thr His Thr Gly
             20                  25

<210> SEQ ID NO 2
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Tyr Lys Cys Ser Glu Cys Gly Lys Ala Phe Ser Gln Lys Ser Asn
 1               5                  10                  15

Leu Thr Arg His Gln Arg Ile His Thr Gly Glu Lys Pro
             20                  25

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 3

Thr Gly Glu Lys Pro
  1               5

<210> SEQ ID NO 4
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: 5-methyl cytosine, Thymine or Cytosine

<400> SEQUENCE: 4 gcggnggcg                                                            9

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Zinc Finger
      peptide

<400> SEQUENCE: 5

Arg Glu Asp Val Leu Ile Arg His Gly Lys
  1               5                  10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Asp Ala Leu Met Val His Lys Arg
  1               5                  10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Arg Gly Pro Asp Leu Ala Arg His Gly Arg
  1               5                  10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Arg Ala Asp Ala Leu Met Val His Lys Arg
  1               5                  10
```

```
<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Arg Gly Pro Asp Leu Ala Arg His Gly Arg
 1               5                  10

<210> SEQ ID NO 10
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Glu Asp Val Leu Ile Arg His Gly Lys
 1               5                  10

<210> SEQ ID NO 11
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
ctcctgcagt tggacctgtg ccatggccgg ctgggccgca tagaatggaa caactaaagc    60

<210> SEQ ID NO 12
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(11)
<223> OTHER INFORMATION: GGMC or GMGC, where M is 5-Methyl Cytosine

<400> SEQUENCE: 12
tatagtgnnn nggcgtgtca cagtcagtcc acacacgtc                           39

<210> SEQ ID NO 13
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13 ggcccggcg                                                             9

<210> SEQ ID NO 14
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
```

```
<400> SEQUENCE: 14 gcgccggcg                                                                    9

<210> SEQ ID NO 15
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 5-Methyl Cytosine

<400> SEQUENCE: 15
tatagtgggn cggcgtgtca cagtcagtcc acacacgtc                                  39

<210> SEQ ID NO 16
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: 5-Methyl Cytosine

<400> SEQUENCE: 16
tatagtggng cggcgtgtca cagtcagtcc acacacgtc                                  39

<210> SEQ ID NO 17
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (10)
<223> OTHER INFORMATION: 5-Methyl Cytosine, Thymine or Cytosine

<400> SEQUENCE: 17
tatagtgggn cggcgtgtca cagtcagtcc acacacgtc                                  39

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (9)
<223> OTHER INFORMATION: 5- Methyl Cytosine, Thymine or Cytosine

<400> SEQUENCE: 18
tatagtggng cggcgtgtca cagtcagtcc acacacgtc                                  39

<210> SEQ ID NO 19
<211> LENGTH: 39
<212> TYPE: DNA
<213> ORGANISM: Artificial Sequence
<220> FEATURE:
```

-continued

<223> OTHER INFORMATION: Description of Artificial Sequence: Synthetic
      oligonucleotide

<400> SEQUENCE: 19
tatagtgggt cggcgtgtca cagtcagtcc acacacgtc                                39

<210> SEQ ID NO 20
<211> LENGTH: 7
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 20

Arg Ser Asp Glu Leu Thr Arg
 1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 21

Arg Ser Asp Glu Leu Thr Arg
 1               5

<210> SEQ ID NO 22
<211> LENGTH: 7
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 22

Arg Ser Asp Glu Leu Thr Arg
 1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 23

Arg Ser Asp Glu Leu Thr Arg
 1               5

<210> SEQ ID NO 24
<211> LENGTH: 7
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 24

Arg Ser Asp Glu Leu Thr Arg
 1               5

<210> SEQ ID NO 25

```
<211> LENGTH: 7
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 25

Arg Ser Asp Asp Leu Ser Gln
  1               5

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 26

Arg Ser Asp Asp Leu Thr Arg
  1               5

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 27

Arg Ser Asp Asp Leu Thr Gly
  1               5

<210> SEQ ID NO 28
<211> LENGTH: 7
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 28

Arg Ser Asp His Leu Ser Ala
  1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 29

Arg Ser Asp Asp Leu Ser Thr
  1               5

<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 30
```

-continued

Arg Lys His His Arg Lys Glu
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 31

Tyr Asp Gly Ala Arg Lys Arg
1               5

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 32

His Asn Arg Asp Arg Lys Arg
1               5

<210> SEQ ID NO 33
<211> LENGTH: 7
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 33

Thr Asn Ser Thr Arg Thr Lys
1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Zinc finger
      peptide

<400> SEQUENCE: 34

Arg Asn Asp His Arg Lys Thr
1               5

<210> SEQ ID NO 35
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)
<223> OTHER INFORMATION: 5-Methyl Cytosine

<400> SEQUENCE: 35 gggncggcg                                                              9

<210> SEQ ID NO 36
<211> LENGTH: 9

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36 gggccggcg                                                              9

<210> SEQ ID NO 37
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 5-Methyl Cytosine

<400> SEQUENCE: 37 ggngcggcg                                                              9

<210> SEQ ID NO 38
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38 ggcgcggcg                                                              9

<210> SEQ ID NO 39
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Met Ala Glu Glu Lys Pro
 1               5

<210> SEQ ID NO 40
<211> LENGTH: 24
<212> TYPE: PRT
<213> ORGANISM: Artificial Sequence
<220> FEATURE:
<223> OTHER INFORMATION: Description of Artificial Sequence: Synthetic
      zinc finger peptide
<220> FEATURE:
<221> NAME/KEY: MOD_RES
<222> LOCATION: (-13)
<223> OTHER INFORMATION: Any amino acid
<220> FEATURE:
<221> NAME/KEY: MOD_RES
<222> LOCATION: (-11)..(-8)
<223> OTHER INFORMATION: Any amino acid and this range may encompass 2-4
      residues
<220> FEATURE:
<221> NAME/KEY: MOD_RES
<222> LOCATION: (-6)..(-4)
<223> OTHER INFORMATION: Any amino acid and this range may encompass 2-3
      residues
<220> FEATURE:
<221> NAME/KEY: MOD_RES
<222> LOCATION: (-2)..(3)
```

```
<223> OTHER INFORMATION: Any amino acid
<220> FEATURE:
<221> NAME/KEY: MOD_RES
<222> LOCATION: (5)..(6)
<223> OTHER INFORMATION: Any amino acid
<220> FEATURE:
<221> NAME/KEY: MOD_RES
<222> LOCATION: (8)..(10)
<223> OTHER INFORMATION: Any amino acid

<400> SEQUENCE: 40

Xaa Cys Xaa Xaa Xaa Xaa Cys Xaa Xaa Xaa Phe Xaa Xaa Xaa Xaa
         -10                  -5                   -1   1

Xaa Leu Xaa Xaa His Xaa Xaa Xaa His
         5                  10

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Thr Gly Glu Lys
  1

<210> SEQ ID NO 42
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (5)
<223> OTHER INFORMATION: Pro may or may not be present

<400> SEQUENCE: 42

Thr Gly Glu Lys Pro
  1               5

<210> SEQ ID NO 43
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43 gcggcggcg                                                          9

<210> SEQ ID NO 44
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44 gcggtggcg                                                          9

<210> SEQ ID NO 45
<211> LENGTH: 9
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45 gcgtgggcg                                                                 9

<210> SEQ ID NO 46
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)
<223> OTHER INFORMATION: 5-Methyl Cytosine

<400> SEQUENCE: 46 gggncggcg                                                                 9

<210> SEQ ID NO 47
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47 gggccggcg                                                                 9

<210> SEQ ID NO 48
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)
<223> OTHER INFORMATION: 5-Methyl Cytosine

<400> SEQUENCE: 48 ggngcggcg                                                                 9

<210> SEQ ID NO 49
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49 ggcgcggcg                                                                 9

<210> SEQ ID NO 50
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
```

```
<221> NAME/KEY: modified_base
<222> LOCATION: (3)
<223> OTHER INFORMATION: 5-Methyl Cytosine

<400> SEQUENCE: 50 ggnccggcg                                                                    9

<210> SEQ ID NO 51
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51 gggtcggcg                                                                    9

<210> SEQ ID NO 52
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52 ggtgcggcg                                                                    9

<210> SEQ ID NO 53
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)
<223> OTHER INFORMATION: 5-Methyl Cytosine

<400> SEQUENCE: 53 gggncggcg                                                                    9

<210> SEQ ID NO 54
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54 gggtcggcg                                                                    9

<210> SEQ ID NO 55
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: 5-Methyl Cytosine

<400> SEQUENCE: 55
```

-continued

```
gcggnggcg                                                              9

<210> SEQ ID NO 56
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 56 gcggccgcg                                                              9

<210> SEQ ID NO 57
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: 5-Methyl Cytosine

<400> SEQUENCE: 57 gcggncgcg                                                              9

<210> SEQ ID NO 58
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)
<223> OTHER INFORMATION: 5-Methyl Cytosine

<400> SEQUENCE: 58 gcggncgcg                                                              9

<210> SEQ ID NO 59
<211> LENGTH: 32
<212> TYPE: PRT
<213> ORGANISM: Artificial Sequence
<220> FEATURE:
<223> OTHER INFORMATION: Description of Artificial Sequence: Zinc Finger
      peptide

<400> SEQUENCE: 59

Met Ala Glu Glu Arg Pro Tyr Ala Cys Pro Val Glu Ser Cys Asp Arg
 1               5                  10                  15

Arg Phe Ser Arg Ser Asp Glu Leu Thr Arg His Ile Arg Ile His Thr
             20                  25                  30

<210> SEQ ID NO 60
<211> LENGTH: 28
<212> TYPE: PRT
<213> ORGANISM: Artificial Sequence
<220> FEATURE:
<223> OTHER INFORMATION: Description of Artificial Sequence: Zinc Finger
      peptide
<220> FEATURE:
<221> NAME/KEY: MOD_RES
<222> LOCATION: (16)..(19)
<223> OTHER INFORMATION: Any amino acid
<220> FEATURE:
```

```
<221> NAME/KEY: MOD_RES
<222> LOCATION: (21)..(22)
<223> OTHER INFORMATION: Any amino acid
<220> FEATURE:
<221> NAME/KEY: MOD_RES
<222> LOCATION: (24)
<223> OTHER INFORMATION: Any amino acid
<220> FEATURE:
<221> NAME/KEY: MOD_RES
<222> LOCATION: (25)
<223> OTHER INFORMATION: Arg or Lys

<400> SEQUENCE: 60

Gly Gln Lys Pro Phe Gln Cys Arg Ile Cys Met Arg Asn Phe Ser Xaa
 1               5                  10                  15

Xaa Xaa Xaa Leu Xaa Xaa His Xaa Xaa Thr His Thr
            20                  25

<210> SEQ ID NO 61
<211> LENGTH: 32
<212> TYPE: PRT
<213> ORGANISM: Artificial Sequence
<220> FEATURE:
<223> OTHER INFORMATION: Description of Artificial Sequence: Zinc Finger
      peptide

<400> SEQUENCE: 61

Gly Glu Lys Pro Phe Ala Cys Asp Ile Cys Gly Arg Lys Phe Ala Arg
 1               5                  10                  15

Ser Asp Glu Arg Lys Arg His Thr Lys Ile His Leu Arg Gln Lys Asp
            20                  25                  30

<210> SEQ ID NO 62
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Arg Gly Asp Ala Leu Thr Ser His Glu Arg
 1               5                  10

<210> SEQ ID NO 63
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Arg Val Asp Ala Leu Glu Ala His Arg Arg
 1               5                  10

<210> SEQ ID NO 64
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Arg Glu Asp Ala Leu Ile Arg His Gly Lys
 1               5                  10
```

```
<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Zinc Finger
      peptide

<400> SEQUENCE: 65

Glu Lys Arg His His Lys Arg
 1               5

<210> SEQ ID NO 66
<211> LENGTH: 4
<212> TYPE: PRT
<213> ORGANISM: Artificial Sequence
<220> FEATURE:
<223> OTHER INFORMATION: Description of Artificial Sequence: Zinc Finger
      peptide

<400> SEQUENCE: 66

Gln Ser Leu Asp
 1

<210> SEQ ID NO 67
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)
<223> OTHER INFORMATION: 5-Methyl Cytosine

<400> SEQUENCE: 67
gacgtgtgga ctgactgtga cacgccggnc cactata                        37

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Zinc Finger
      peptide

<400> SEQUENCE: 68

Arg Lys Arg Ala Gly Asp Tyr
 1               5

<210> SEQ ID NO 69
<211> LENGTH: 4
<212> TYPE: PRT
<213> ORGANISM: Artificial Sequence
<220> FEATURE:
<223> OTHER INFORMATION: Description of Artificial Sequence: Zinc Finger
      peptide

<400> SEQUENCE: 69

Arg Thr Leu Asp
 1

<210> SEQ ID NO 70
<211> LENGTH: 37
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (29)
<223> OTHER INFORMATION: 5-Methyl Cytosine

<400> SEQUENCE: 70
gacgtgtgga ctgactgtga cacgccgrnc cactata                              37

<210> SEQ ID NO 71
<211> LENGTH: 7
<212> TYPE: PRT
<213> ORGANISM: Artificial Sequence
<220> FEATURE:
<223> OTHER INFORMATION: Description of Artificial Sequence: Zinc Finger
      peptide

<400> SEQUENCE: 71

Arg Lys Arg Asp Arg Asn His
  1               5

<210> SEQ ID NO 72
<211> LENGTH: 4
<212> TYPE: PRT
<213> ORGANISM: Artificial Sequence
<220> FEATURE:
<223> OTHER INFORMATION: Description of Artificial Sequence: Zinc Finger
      peptide

<400> SEQUENCE: 72

Gly Thr Leu Asp
  1

<210> SEQ ID NO 73
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (29)
<223> OTHER INFORMATION: 5-Methyl Cytosine

<400> SEQUENCE: 73
gacgtgtgga ctgactgtga cacgccgrnc cactata                              37

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Zinc Finger
      peptide

<400> SEQUENCE: 74

Lys Thr Arg Thr Ser Asn Thr
  1               5

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Zinc Finger
      peptide
```

```
<400> SEQUENCE: 75

Ala Ser Leu His
  1

<210> SEQ ID NO 76
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (28)
<223> OTHER INFORMATION: 5-Methyl Cytosine

<400> SEQUENCE: 76
gacgtgtgga ctgactgtga cacgccgnrc cactata                              37

<210> SEQ ID NO 77
<211> LENGTH: 7
<212> TYPE: PRT
<213> ORGANISM: Artificial Sequence
<220> FEATURE:
<223> OTHER INFORMATION: Description of Artificial Sequence: Zinc Finger
      peptide

<400> SEQUENCE: 77

Thr Lys Arg His Asp Asn Arg
  1               5

<210> SEQ ID NO 78
<211> LENGTH: 4
<212> TYPE: PRT
<213> ORGANISM: Artificial Sequence
<220> FEATURE:
<223> OTHER INFORMATION: Description of Artificial Sequence: Zinc Finger
      peptide

<400> SEQUENCE: 78

Thr Ser Leu Asp
  1

<210> SEQ ID NO 79
<211> LENGTH: 37
<212> TYPE: DNA
<213> ORGANISM: Artificial Sequence
<220> FEATURE:
<223> OTHER INFORMATION: Description of Artificial Sequence: Synthteic
      oligonucleotide
<220> FEATURE:
<221> NAME/KEY: modified_base
<222> LOCATION: (29)
<223> OTHER INFORMATION: 5-Methyl Cytosine

<400> SEQUENCE: 79
gacgtgtgga ctgactgtga cacgccganc cactata                              37

<210> SEQ ID NO 80
<211> LENGTH: 60
<212> TYPE: DNA
<213> ORGANISM: Artificial Sequence
<220> FEATURE:
<223> OTHER INFORMATION: Description of Artificial Sequence: Synthetic
      nucleotide sequence

<400> SEQUENCE: 80
tatagtggcg cggcgtgtca cagtcaggtg ggccggcgtg tcacagtcag tccacacgtc     60
```

```
<210> SEQ ID NO 81
<211> LENGTH: 31
<212> TYPE: PRT
<213> ORGANISM: Artificial Sequence
<220> FEATURE:
<223> OTHER INFORMATION: Description of Artificial Sequence: Synthetic
      zinc finger peptide
<220> FEATURE:
<221> NAME/KEY: MOD_RES
<222> LOCATION: (1)..(2)
<223> OTHER INFORMATION: Any amino acid and this range may encompass 0-2
      residues
<220> FEATURE:
<221> NAME/KEY: MOD_RES
<222> LOCATION: (4)..(8)
<223> OTHER INFORMATION: Any amino acid and this range may encompass 1-5
      residues
<220> FEATURE:
<221> NAME/KEY: MOD_RES
<222> LOCATION: (10)..(23)
<223> OTHER INFORMATION: Any amino acid and this range may encompass
      9-14 residues
<220> FEATURE:
<221> NAME/KEY: MOD_RES
<222> LOCATION: (25)..(30)
<223> OTHER INFORMATION: Any amino acid and this range may encompass 3-6
      residues
<220> FEATURE:
<221> NAME/KEY: MOD_RES
<222> LOCATION: (31)
<223> OTHER INFORMATION: Xaa is Histidine or Cysteine

<400> SEQUENCE: 81

Xaa Xaa Cys Xaa Xaa Xaa Xaa Xaa Cys Xaa Xaa Xaa Xaa Xaa Xaa Xaa
 1               5                  10                  15

Xaa Xaa Xaa Xaa Xaa Xaa Xaa His Xaa Xaa Xaa Xaa Xaa Xaa Xaa
            20                  25                  30
```